United States Patent
Weleber et al.

(10) Patent No.: US 8,657,446 B2
(45) Date of Patent: Feb. 25, 2014

(54) METHOD AND APPARATUS FOR VISUAL FIELD MONITORING

(75) Inventors: Richard G. Weleber, Portland, OR (US); Richard E. Crandall, Portland, OR (US); Scott P. Gillespie, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 73 days.

(21) Appl. No.: 13/125,627

(22) PCT Filed: Oct. 28, 2009

(86) PCT No.: PCT/US2009/062427
§ 371 (c)(1),
(2), (4) Date: Apr. 22, 2011

(87) PCT Pub. No.: WO2010/053800
PCT Pub. Date: May 14, 2010

(65) Prior Publication Data
US 2011/0194075 A1   Aug. 11, 2011

Related U.S. Application Data

(60) Provisional application No. 61/109,155, filed on Oct. 28, 2008, provisional application No. 61/175,415, filed on May 4, 2009.

(51) Int. Cl.
*A61B 3/00* (2006.01)
(52) U.S. Cl.
USPC .......................................... 351/246; 351/205
(58) Field of Classification Search
USPC .......................................... 351/205, 246, 200
See application file for complete search history.

(56) References Cited

U.S. PATENT DOCUMENTS

| | | | |
|---|---|---|---|
| 5,864,385 A | 1/1999 | Gonzales de la Rosa | |
| 2003/0206686 A1* | 11/2003 | Pau et al. | 385/18 |
| 2004/0057013 A1 | 3/2004 | Cappo et al. | |
| 2008/0108894 A1 | 5/2008 | Elgavish et al. | |

OTHER PUBLICATIONS

Schiefer, U. et al., "Conventional Perimetry I: Introduction—basics," Ophthalmologe, 2005; vol. 102, pp. 627-646.
Schiefer, U. et al., "Comparison of the New Perimetric German Adaptive Threshold Estimation: (GATE) Stretegy with Conventional Full-Threshold and SITA Standard Strategies," Investigative Ophthalmology and Visual Science, 2009, vol. 50, pp. 488-494.
Hermann, A. et al., "Age-Dependent Normative Values for Differential Luminance Sensitivity in Automated Static Perimetry Using the Octopus 101," Acta Ophthalmologica, 2008, vol. 86, pp. 446-455.
Schiller, J. et al., "Quantification of Stato-Kinetic Dissociation by Semi-Automated Perimetry," Vision Research, 2006, vol. 46, pp. 117-128.
Mc Kay, G. et al., "Pigmented Paravenous Chorioretinalatrophy is Associated with a Mutation with the Crumbs homolog 1 (CRB1) Gene" Invest Ophthalmol Vis Sci, 2005, vol. 46, pp. 332-328.
University of Illinois Eye & Ear Infirmary, "Aging Eye Times," 2003.

* cited by examiner

*Primary Examiner* — Hung Dang
(74) *Attorney, Agent, or Firm* — Schwabe, Williamson & Wyatt

(57) ABSTRACT

Embodiments provide methods and systems for the modeling and analysis of visual fields. Methods for global and regional measurement of visual sensitivity and quantification of field loss are provided in accordance with various embodiments. Further embodiments provide systems and methods for the diagnosis of diseases affecting the visual field. In addition, embodiments provide methods and systems for measuring and quantifying the volume of the Hill of Vision for an individual subject.

27 Claims, 32 Drawing Sheets

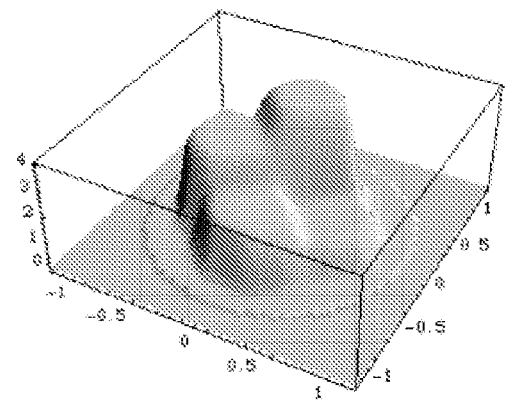
Fig. 4
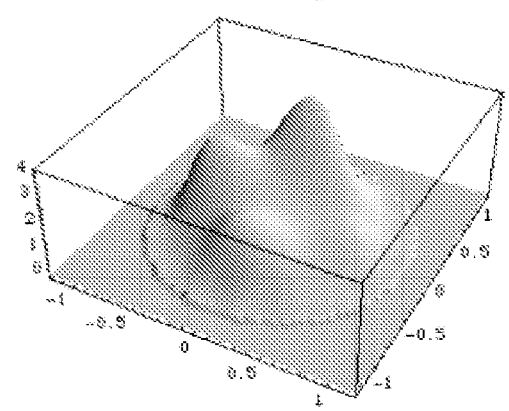
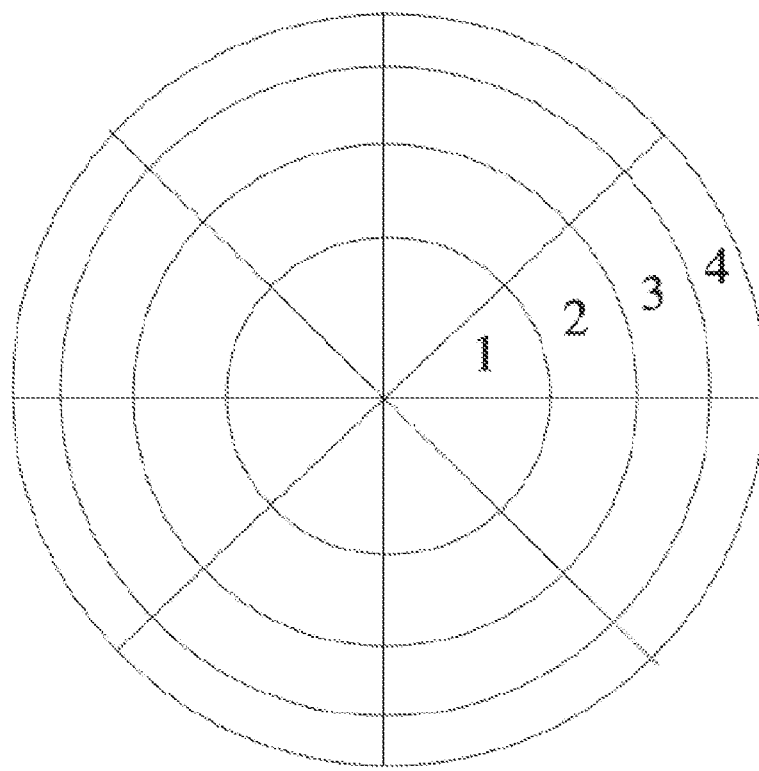
Fig. 5

Fig. 20A
Fig. 20B
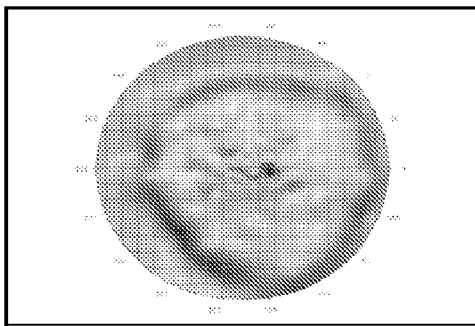
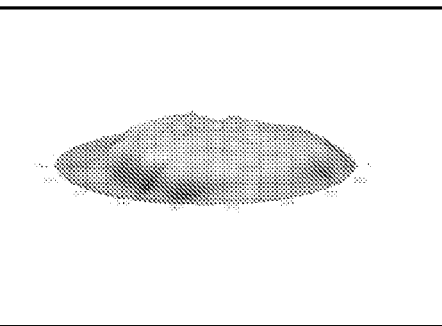
Fig. 20C
Fig. 20D
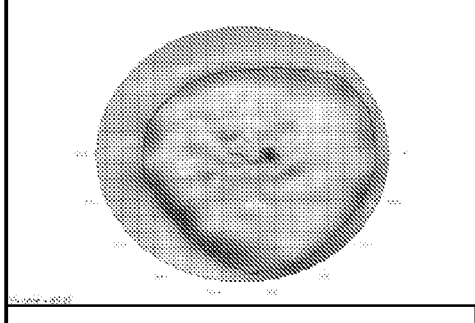
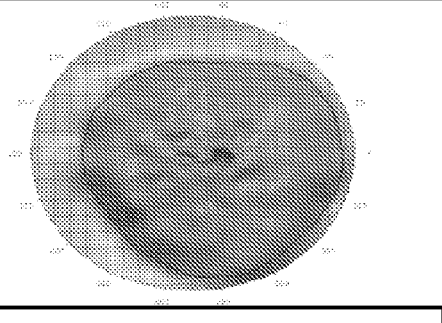
Fig. 20E
Fig. 20F
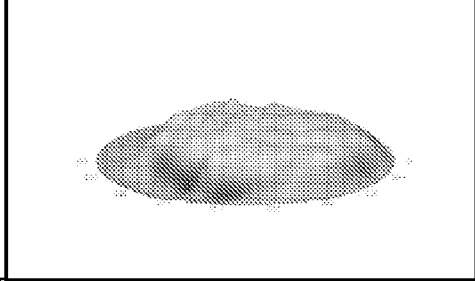
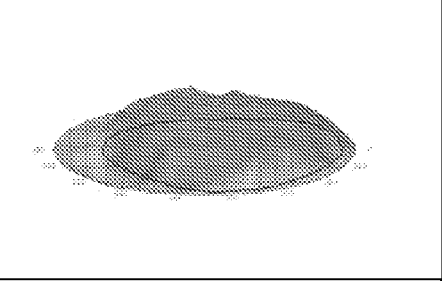
Fig. 20G
Fig. 20H
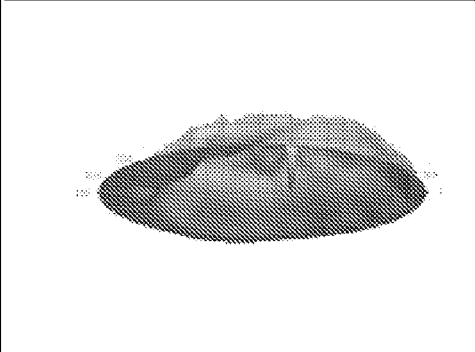
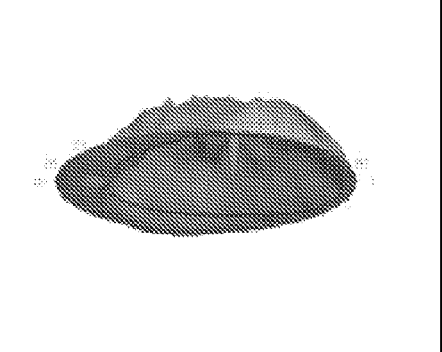

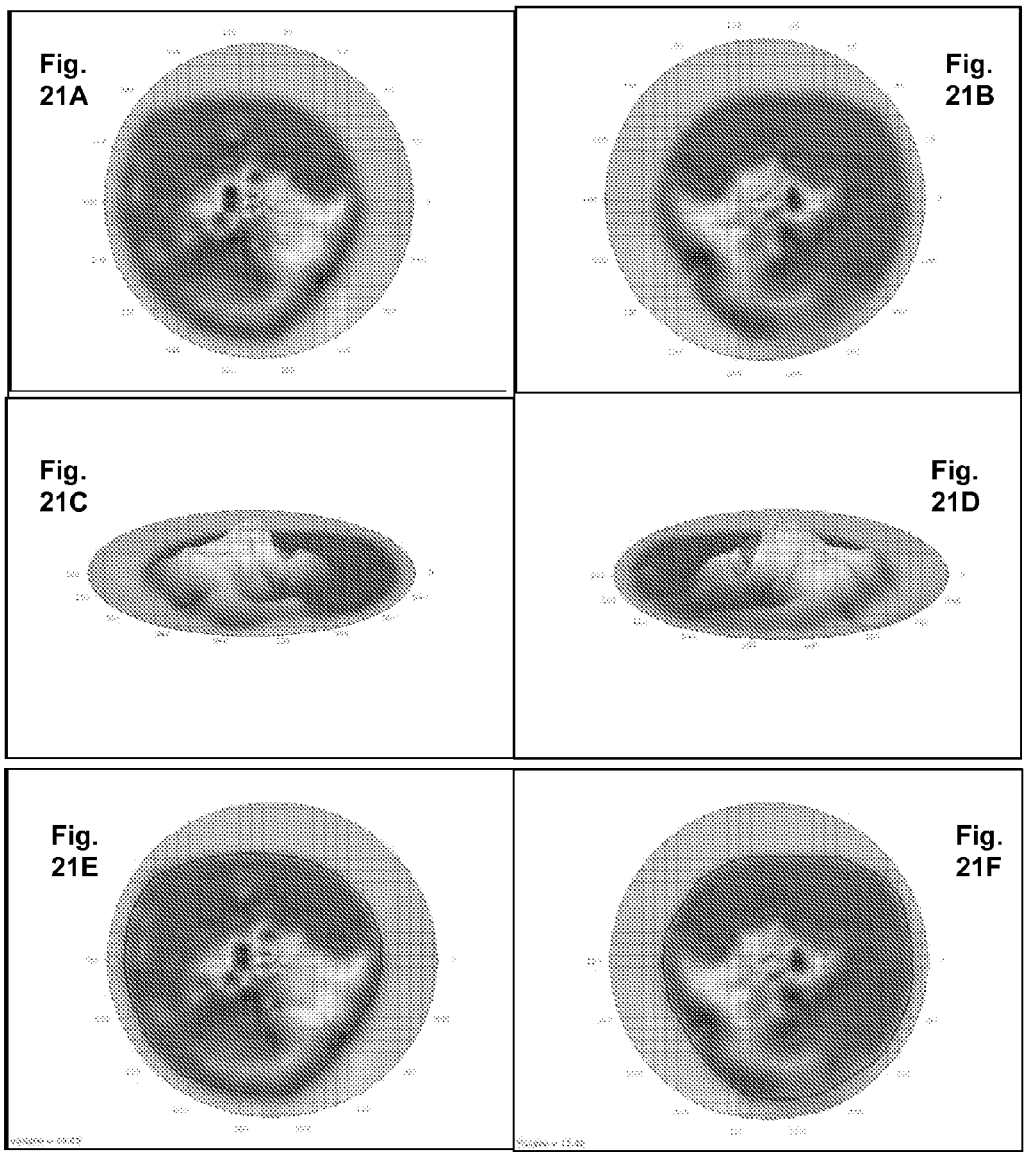

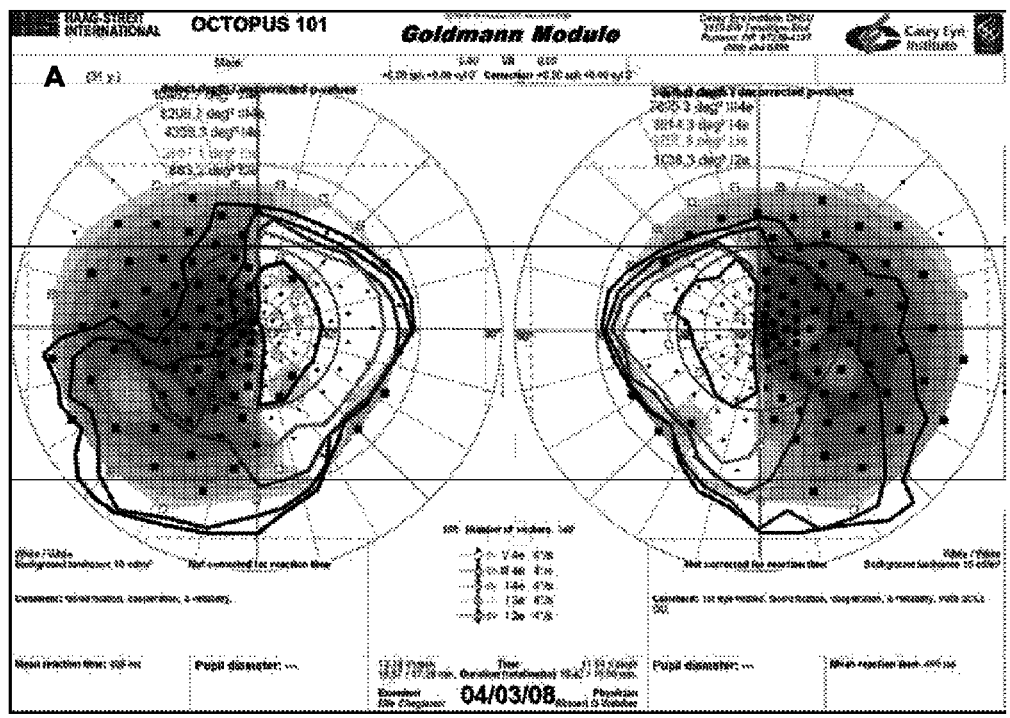
Fig. 27A
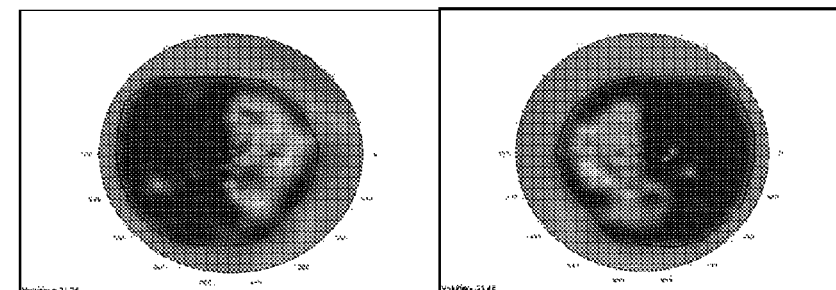
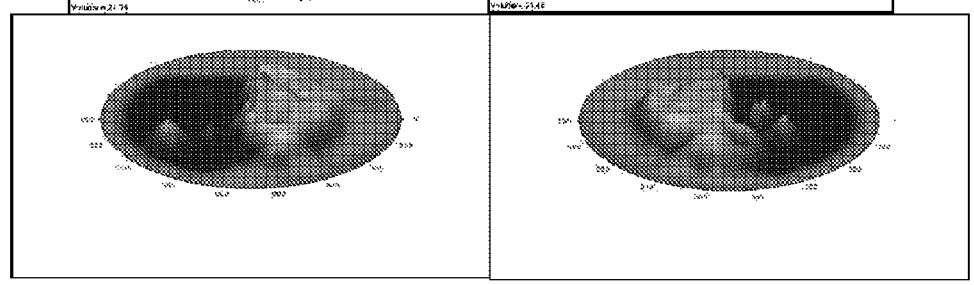
Fig. 27B  Fig. 27C
Fig. 27D  Fig. 27E

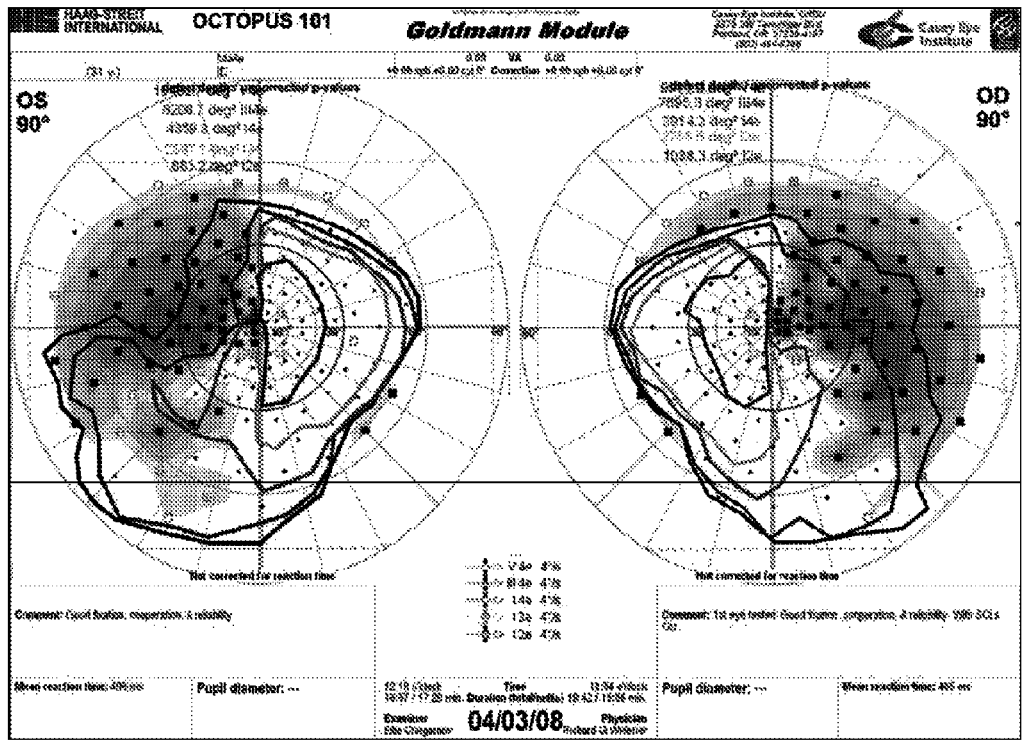
Fig. 28A
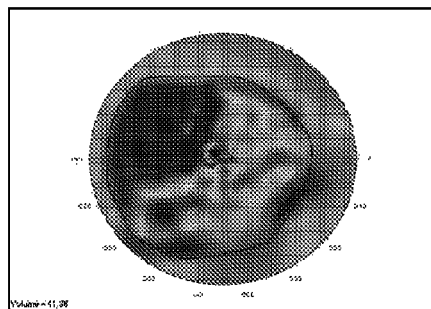
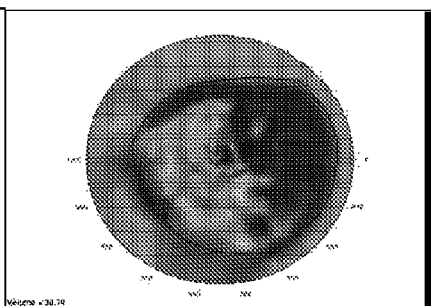
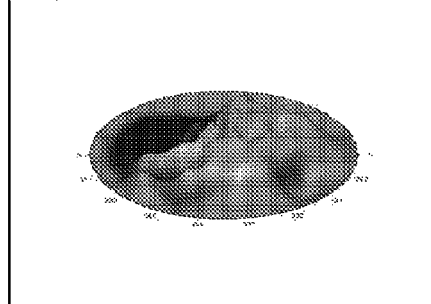
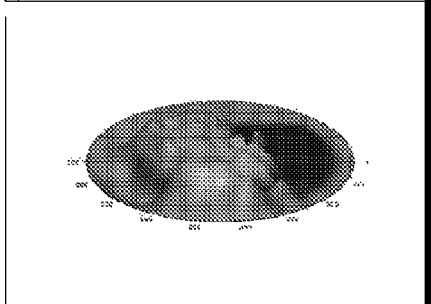
Fig. 28B
Fig. 28C
Fig. 28D
Fig. 28E Fig. 29A
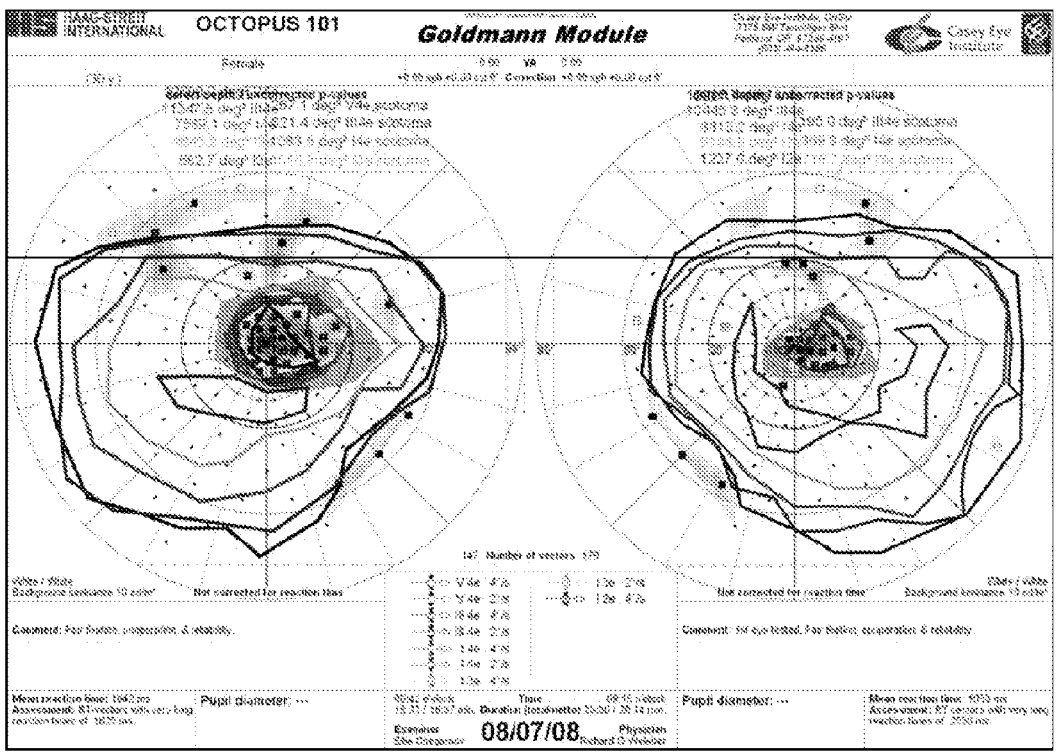
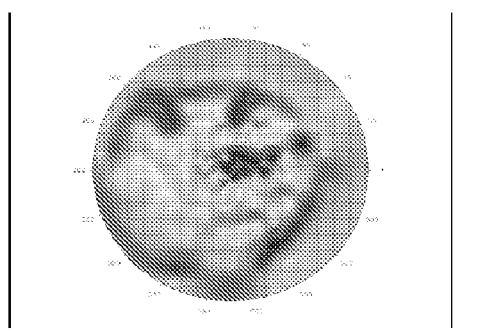    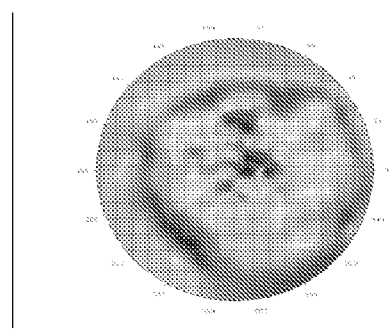
Fig. 29B                Fig. 29C Fig. 29L
Fig. 29M
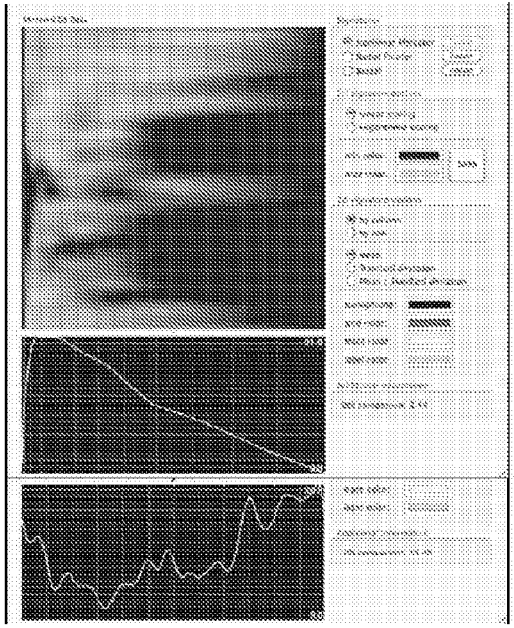
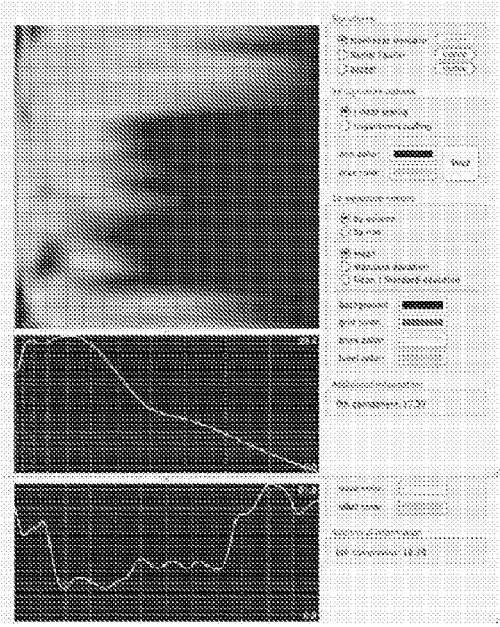
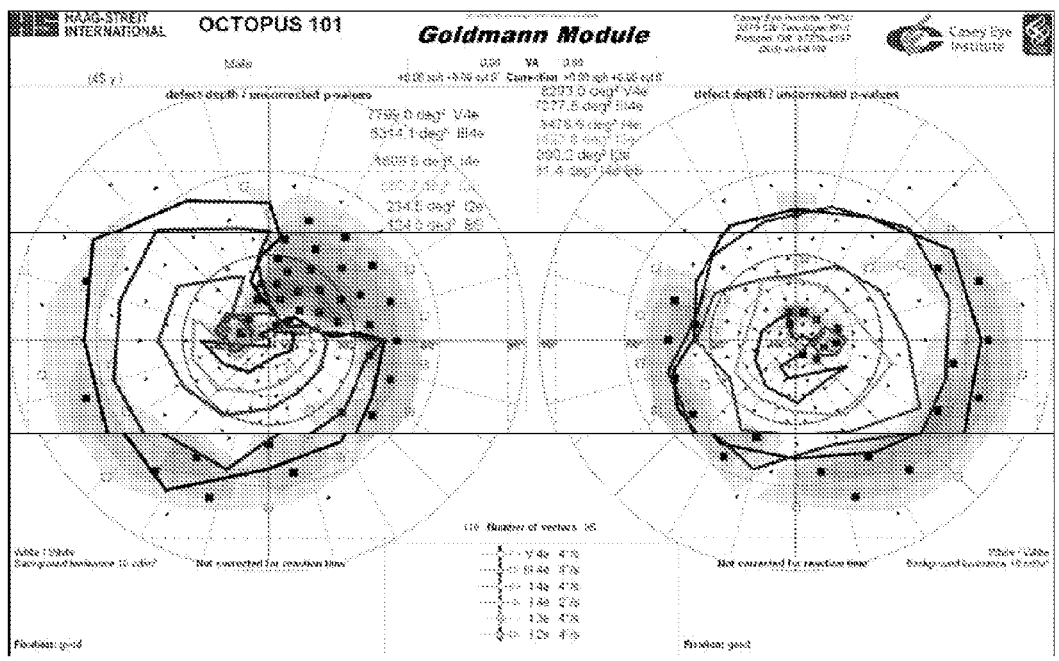
Fig. 30

Fig. 32A
Fig. 32B
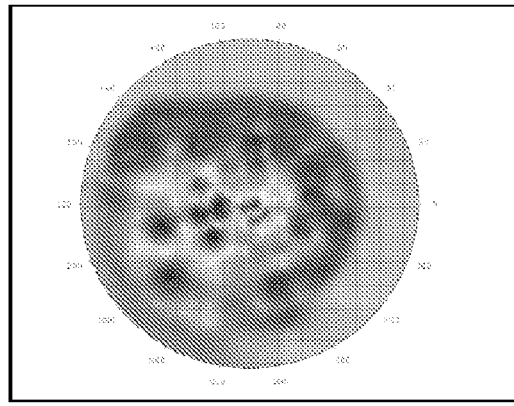
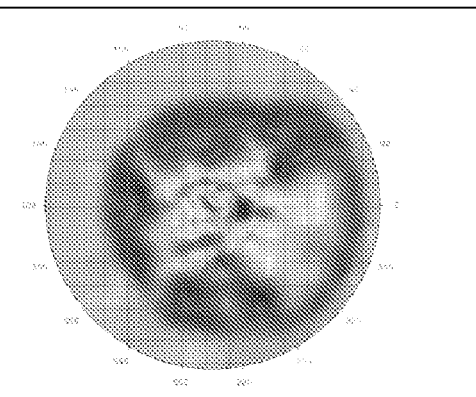
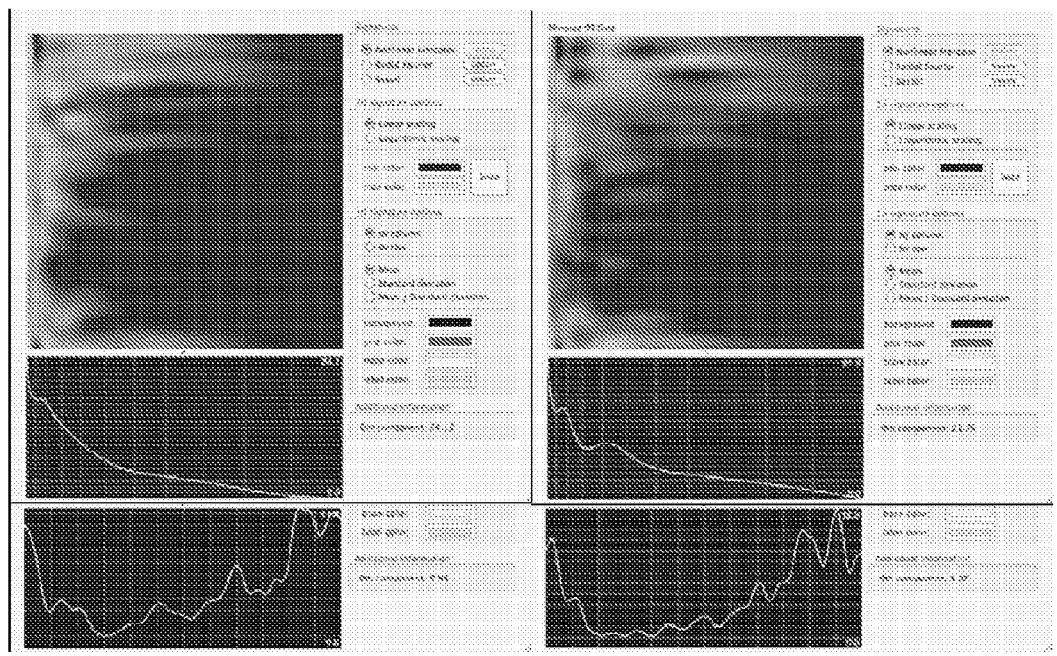
Fig. 32C
Fig. 32D

METHOD AND APPARATUS FOR VISUAL FIELD MONITORING

CROSS REFERENCE TO RELATED APPLICATIONS

The present application claims priority to U.S. Provisional Patent Application No. 61/109,155, filed Oct. 28, 2008, entitled "VISUAL FIELD MODELING AND ANALYSIS SYSTEMS AND METHODS," and U.S. Provisional Patent Application No. 61/175,415, filed May 4, 2009, entitled "METHOD AND APPARATUS FOR VISUAL FIELD MONITORING," both of which are hereby incorporated by reference in their entirety.

TECHNICAL FIELD

Embodiments herein relate to the field of visual field modeling and analysis, and, more specifically, to the analysis of visual sensitivity using static perimetry for the diagnosis and characterization of visual defects.

BACKGROUND

The visual field is that physical space, measured in degrees eccentric to fixation, in which the human eye can perceive images and detect motion. Many causes, ranging from trauma, infection, cancer, autoimmune diseases, toxins, degeneration, or genetic etiology, can alter or disturb the visual field, often in specific, characteristic ways. Diagnosis of the precise, underlying cause of the loss of visual field and characterization of the nature and extent of the loss is essential for prognosis of, and analysis of treatments for, these conditions.

Kinetic visual field testing (perimetry) of the full visual field is commonly used to determine the visual field of subjects with retinitis pigmentosa (RP). Kinetic perimetry utilizes a moving test target, and is time-consuming, dependent upon the availability of a skilled perimetrist, and difficult to quantify, which limits its usefulness in monitoring disease progression and treatment efficacy. By contrast, full-threshold static perimetry, in which retinal sensitivity is measured at multiple stationary test sites in the visual field, is much more objective, can be performed by a wider array of technical personnel, and produces digital data that are suitable for statistical analysis. However, whereas this approach has the advantage of reducing the data to a single variable (the mean deviation [MD], which is a quantitative variable designating overall retinal sensitivity), all topographic information about the location where the visual field changes exist or are changing with time, is lost.

The progression of RP within the retina is far from uniform, and midperipheral regions are the most likely to sustain the earliest and most severe damage. The disease, in most cases, progresses in a symmetrical fashion when examined along temporal-to-nasal and superior-to-inferior axes; thus, any deviation from this expected natural history is lost using a single parameter such as the mean deviation. Special, fast static perimetry programs exist for glaucoma (e.g., the SITA and other Bayesian probability-based threshold determination algorithms and test strategies), but the spatial characteristics and progression of field defects in RP are very different from those of glaucoma. Conventional, full-threshold static perimetry algorithms can assess visual fields in subjects with RP, but the time involved to test each eye is often double that necessary for the more rapid SITA algorithms designed for glaucoma. This increased testing time adds to subject fatigue and decreases the reliability of the data. Test-retest variability is a major limitation in visual field testing, and as a result, limits the usefulness of SITA for monitoring RP.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 4 illustrates two splines passing (very nearly) through heights 1, 2, 3, 4 at given input positions, in accordance with various embodiments. S has been artificially forced to be slightly negative outside the unit circle, to show the effects of the forced boundary zeros. The top spline surface uses a Yukawa form with L:=5, ϵ:=0.00005, α:=3. The bottom spline surface uses L:=2, ϵ:=0.00005, α:=1.

FIG. 5 illustrates how the nonlinear-Mercator transformation decimates the unit disk into lines of latitude (radius) and longitude (azimuthal angle), except that discrete radii are used in such a way that all incremental areas are equal, in accordance with various embodiments. The unit disk has been decimated into 32 regions, where sectors 1, 2, 3, 4, and therefore all 32 sectors, all have the same area.

FIG. 17 includes two panels illustrating the use of the W187 grid and size III and V test targets, in accordance with various embodiments.

FIG. 19A shows three-dimensional plots of the HOV for a 9-year-old subject with Usher Syndrome Type I with only one mutation of MYO7A of uncertain significance (molecular testing was inconclusive), and FIG. 19B shows three-dimensional plots (left), Mercator projections (top graphs), and Signatures (2 lowest graphs) of the fields of vision using the size V test target of the subject with Usher syndrome shown in FIGS. 17B and 18 (upper left) with two disease-defining mutations of MYO7A and the right eye of the subject with Usher syndrome shown in FIG. 19A (below, right).

FIGS. 20A-H are panels that illustrate volumetric measurements of the HOV for the right eye of a normal subject, in accordance with various embodiments. FIGS. 20A (top left) and 20B (top right) show en face and side views of the HOV of a normal subject using the W187 grid and the size III test target. FIGS. 20C (second row, left) and 20D (second row right) illustrate the use of a selection tool within VFMA to measure the volume of the entire HOV. FIGS. 20E (third row, left) and 20F (third row, right) show side views of the selection shown in FIGS. 20C and 20D, respectively. FIGS. 20G (bottom row, left) and 20H (bottom row, right) show additional side views of the selection shown in FIGS. 20C and 20D.

FIGS. 21A-F are panels illustrating three-dimensional graphs of the HOV for the left (left) and right (right) eyes of a subject with RP, in accordance with various embodiments. FIGS. 21A (top row, left) and 21B (top row, right) show en face views of the HOV for the left and right eyes, respectively, of a subject with RP. FIGS. 21B (second row, left) and 21C (second row, right) show side views of the HOV for the left and right eyes, respectively, of a subject with RP. FIGS. 21E (third row, left) and 21F (third row, right) show use of a selection tool within VMFA to measure the volume of the HOV for the left and right eyes, respectively, of a subject with RP.

FIGS. 22A (top row, left) and 22B (top row, right) show tilt views of the selected HOV for the left and right eyes, respectively, of a subject with RP. FIGS. 22C (middle row, left) and 22D (middle row, right) show side views of the selected HOV for the left and right eyes, respectively, of a subject with RP. FIGS. 22D (bottom row, left) and 22E (bottom row, right) show side views of the HOV for the left and right eyes, respectively, of a subject with RP.

FIGS. 23A-G are panels illustrating use of a selection tool within VMFA to determine volumetric measurements of specific areas of the HOV and for mathematical signatures on these selections, in accordance with various embodiments. FIGS. 23A (top row, left) and 23B (top row, right) show selection of circles within a visual field. FIGS. 23C (second row, left) and 23D show side views of the selection shown in FIGS. 23A and 23B, respectively. FIGS. 23E (third row, left) and 23F (third row, right) show use of the selection tool to place similar sized circles in different areas of the HOV to measure the sensitivity in those regions. FIG. 23G (bottom row, center) shows a measurement of a specific area within the HOV.

FIG. 24A shows a static perimetry visual field within VMFA of secondary pigmentary retinopathy from the same subject (right side of figure). FIGS. 24B (left) and 24C (right) illustrate en face views of the HOV for the same subject. FIGS. 24D (left) and 24E (right) illustrate side views of the HOV for the same subject.

FIGS. 27A-E are panels showing views of a static perimetry visual field and HOV within VMFA of a 31-year-old subject after neurosurgical removal of a large pituitary tumor that had compressed the chiasm, causing a complete bitemporal hemianopsia, using a size III test target, in accordance with various embodiments. FIG. 27A (top) shows a view of a static perimetry visual field of the same subject. FIGS. 27B (middle row, left) and 27C (middle row, right) show en face views of the HOV of the same subject's left and right eyes, respectively. FIGS. 27D (bottom row, left) and 27E (bottom row, right) show tilt views of the HOV of the same subject's left and right eyes, respectively.

FIGS. 28A-E are panels illustrating views of a static perimetry visual field and HOV within VMFA of the same subject using a size V test target, which may be used to measure lower levels of sensitivity within a field of vision, in accordance with various embodiments. FIG. 28A (top) shows a view of a static perimetry visual field of the subject. FIGS. 28B (middle row, left) and 28C (middle row, right) show en face views of the HOV of the same subject's left and right eyes, respectively. FIGS. 28D (bottom row, left) and 28E (bottom row, right) show tilt views of the HOV of the same subject's left and right eyes, respectively.

FIGS. 29A-M panels showing graphs from a subject with Leber Hereditary Optic Neuropathy, demonstrating how the three-dimensional plots and signatures provided by various embodiments provide additional information helpful to understanding disease at the visual field defect level, in accordance with various embodiments. FIG. 29A (top) shows a view of a static perimetry visual field of the subject. FIGS. 29B (bottom row, left) and 29C (bottom row, right) show en face views of the HOV of the subject's left and right eyes, respectively. FIGS. 29D (top row, left) and 29F (second row, left) show tilt views of the HOV of the same subject's left eye. FIGS. 29E (top row, right) and 29G (second row, right) show tilt views of the HOV of the same subject's right eye. FIGS. 29H (third row, left) and 29I (third row, right) show use of a selection tool within VMFA to select a circle encompassing the central portion of the visual field for the left and right eye, respectively. FIGS. 29J (bottom row, left) and 29K (bottom row, right) show the underside of the HOV and the sensitivity losses within the central field from the disease for the left and right eye, respectively. FIGS. 29L (left) and 29M (right) show Mercator projections and signatures within VMFA showing sensitivity losses from the disease for the left and right eye, respectively.

FIG. 30 shows a static perimetry visual field within VMFA of a subject with both glaucoma and autoimmune retinopathy, for which three-dimensional modeling and analysis of signatures provided by various embodiments offers the ability to quantitate the loss of vision from each component of this person's disease.

FIGS. 32A-D are panels showing graphs within VMFA from the same subject as in FIG. 31, illustrating the HOV in the subject's left (FIG. 32A, top left) and right (FIG. 32B, top right) and the corresponding Mercator projections and signatures (FIG. 32C, bottom left, and FIG. 32D, bottom right, respectively), in accordance with various embodiments.

DETAILED DESCRIPTION OF DISCLOSED EMBODIMENTS

Figure 1:
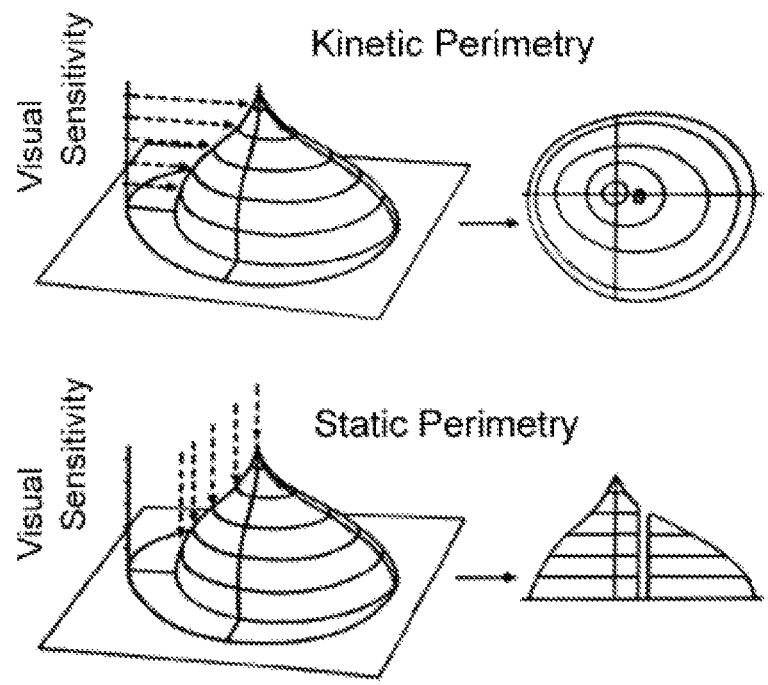
FIG. 1 illustrates perimetry nomenclature: static perimetry, whereby sensitivity at specific retinal locations is determined as the threshold of perception, and kinetic perimetry, which utilizes a moving test target, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments, are synonymous.

In various embodiments, methods, apparatuses, and systems are provided for characterizing the nature and severity of visual defects, for diagnosis of visual defects and disorders impacting vision, and for providing outcome measures in treatment trials for retinal diseases such as retinitis pigmentosa (RP) and other disorders affecting the visual field. Some embodiments provide methods for visual field mapping. The visual field has been characterized as "a hill of vision surrounded by a sea of blindness". As described herein, this Hill of Vision, or HOV, may be mapped in three dimensions in accordance with various embodiments. Such three-dimensional HOV maps may provide detailed models of the visual field, and may enable detailed analysis of visual field defects. Embodiments provide methods and systems for this modeling and analysis.

RP is a hereditary disorder that leads to progressive loss of vision. Although central vision may be affected at any age, the earliest and most disabling visual impairment in RP often is progressive loss of vision in the peripheral field. Accurate monitoring of retinal function in RP requires the use of multiple test methods, including assessment of the visual field to quantify visual field loss.

The "gold standard" of static visual field testing is the full-threshold testing algorithm, in which the sensitivity of every point in the visual field is checked and rechecked methodically, employing recursive staircase increments and decrements in light sensitivity until an endpoint estimate is achieved. This test is extremely time-consuming and tiring for the subject, resulting in decreased reliability of results, and its use would greatly extend the time required for clinical evaluation. A faster testing algorithm that employs statistical forecasting procedures, the Swedish Interactive Testing Algorithm (SITA), was developed for glaucoma to obtain threshold estimates of the same validity and accuracy with a greatly reduced testing time, and this test is now widely used in clinics and in clinical trials. This SITA strategy is designed to accurately detect field loss secondary to glaucoma, however, and is not optimally efficient, accurate, or suitable for testing subjects with RP.

Provided herein are efficient and accurate methods for global and regional measurement of visual sensitivity and visual field loss. Embodiments provide systems and methods for the diagnosis of diseases affecting the visual field. In an exemplary embodiment, methods of visual field mapping are provided that include importing threshold data from an input source, converting the threshold data to constraints on a spline surface with an algorithm, and displaying one or more three-dimensional representations of the subject's HOV. The methods may enable, in some embodiments, the efficient collection of static sensitivity data using a polar-oriented grid. Such HOV mapping may, in some embodiments, permit the diagnosis of a visual field defect, such as those associated with RP, macular degeneration, retinopathy, cancer of the visual system, or injury to the retina or optic nerves.

The HOV has been modeled in the past, most often with pooled data from many normal subjects using powerful mainframe computers, but it has never before been able to be performed as a routine part of every patient evaluation for visual field testing. Nor has the volume of the entire HOV, or selected part or area of the HOV, ever been measured as an indication of the sensitivity of the eye, either for diagnosis or as endpoints for clinical treatment or trials. Indeed, embodiments may uniquely define the unit of the volume of the HOV for measurement as the decibel-steradian (dBsr).

In exemplary embodiments, a computing system may be endowed with one or more components of the disclosed apparatuses and/or systems and may be employed to perform one or more methods as disclosed herein. For instance, in some embodiments, a computer application referred to as VFMA (Visual Field Modeling and Analysis) is disclosed, which allows clinicians and technicians the ability to graph visual field data in unlimited three-dimensional views and to perform several sophisticated mathematical analyses. In embodiments, the units of the HOV are defined, and methods, systems and apparatuses are provided to measure the entire HOV or any selected part.

Particular embodiments provide an application that runs on a Macintosh computer, for instance using OS 10, and that imports "Schwelle" or threshold data from a perimeter, for instance an Octopus 101 or Octopus 900 perimetry apparatus. In other embodiments, one or more components may be programmed to import similar data from other computers or perimetry apparatuses. In embodiments, the threshold data are converted to differential light sensitivity values for display, three-dimensional plotting of the HOV, signature analysis by a number of mathematical functions which are described below in greater detail, and measurement tools to assess the volume of the HOV. In embodiments, the modeling and analysis may include pattern recognition that permits the detection and quantification of the earliest and most disease-specific features of visual field defects. Embodiments may thus establish a new standard of computerized static and kinetic visual field test methodology for the assessment of visual fields of subjects with RP and other visual field disorders or conditions.

While the application of VFMA and the algorithms/functions therein (discussed below) are applicable to the group of genetic disorders of the retina called retinitis pigmentosa (RP), the application VFMA and the algorithms therein are also applicable to evaluation of visual field loss from any cause. Therefore, embodiments provide methods, apparatuses and systems for the characterization of visual defects occurring from any disorder, disease, injury, or other cause of visual field loss. In various examples, the visual field and its three-dimensional representation, the HOV, may become abnormal in many diseases and disorders that affect the visual system, extending from the retina, through the optic nerve, chiasm, optic tract, and radiation to the primary and secondary visual cortical regions where the field of vision and images are reconstructed and interpreted by the brain. The methods of modeling and analysis of the HOV disclosed in various embodiments may be useful for early detection, characterization, and quantification of visual field defects. Specifically, particular embodiments are directed to mathematical signatures that may be condensations of a plurality of HOV measurements.

In embodiments, the HOV (see, e.g., FIG. 1) generally may be assessed by either moving test targets, called kinetic perimetry, or through presentation of static stimuli of specific sizes with increasing brightness until the subject perceives the light, a technique termed static perimetry. In various embodiments, full-field static perimetry was performed on normal subjects and subjects with diseases affecting the visual field using an Octopus 101 perimeter (Haag-Streit, Inc., Koeniz, Switzerland) and radially designed, centrally condensed custom grids of up to 187 test locations (or even more) extending from fixation to 80° temporally, 78° inferiorly, 56° nasally, and 56° superiorly, and targets of Goldmann Size III (0.47° diameter) presented on a 10 cd/m$^2$ background. In some embodiments, the test locations on the grid have a rectilinear distribution. In embodiments, thresholds were determined using the German Adaptive Threshold Estimation (GATE) strategy described herein and discussed at greater length below, and were converted to differential luminance sensitivity (DLS) using transformations. In various embodiments, these DLS values were used to model the HOV and to generate mathematical signatures describing the surface of this three-dimensional structure.

In various embodiments, because most of the mathematical signature analysis involves planar calculations in standard polar coordinates (r, φ), a specific transformation may be employed from the spherical retinal surface to a planar circle.

Figure 2:
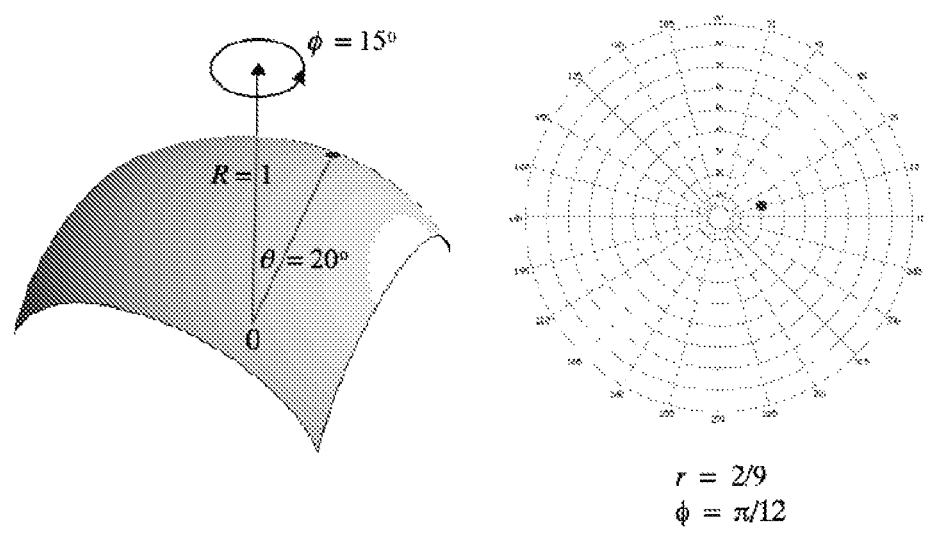
FIG. 2 illustrates spherical signature coordinate transformation, in accordance with various embodiments. Spherical coordinates (R, θ, Φ) for a retinal surface assume R=1, with θ, Φ being the standard polar angle and azimuth. A point of sensitivity measurement (dot on left-hand surface above) is at, say, (R, θ, Φ)=(1, 20°, 15°) on the sphere. The right-hand figure has the measurement point located within a unit circle, at planar polar coordinates (called signature coordinates) r=2/9, corresponding to 2θ/180, and the azimuth in algebraic form, Φ=15/360·2π=π/12.

Referring to FIG. 2, in exemplary embodiments, the (ideal) retinal hemisphere may be modeled via standard spherical coordinates (R, θ, φ)=(1, θ, φ), and so exactly two angular parameters may define a physical location on the retina. As FIG. 2 shows, a location may be mapped to a pair (r, φ), with the caveat that r∈[0, 1] is a geodesic distance along the surface of the hemisphere. Though the original dataset lives on a curved surface, it may be convenient in embodiments to use the final pair of planar coordinates (r, φ), for the algebra of signatures. For example, the Bessel signature disclosed herein may therefore use Bessel arguments of standard, polar form.

In summary, in some embodiments, the signature coordinate system is defined by the transformation:

$$R = 1, \theta, \phi) \rightarrow (r, \phi) := \left(\frac{2\theta}{\pi}, \phi\right),$$

so that the radius r in the resulting planar signature space runs over [0, 1] while the azimuth runs over (−π,π).

In embodiments, when using the planar-polar system (right-hand view in FIG. 2), measurement of arbitrary areas is nontrivial, and may be counter-intuitive. For instance, there may be an exemplary "footprint" shape, e.g., a closed contour drawn in a planar-polar system, and on the full circle there is a dbm-sensitivity function, for instance D(r, φ) but with D vanishing outside the footprint. In many instances, the area of interest is the total integrated D, but integrated over the original retinal surface, e.g., over the back-transformed "footprint." This exemplary total area-sensitivity in units of dB-steradians may appear to be:

$$S \stackrel{?}{=} \iint D(r,\phi) r \, dr \, d\phi,$$

but this is unphysical, incorrect. It is important to take into account the Jacobian curvature factor due to the transformation from spherical to planar-polar, with the correct integral given by:

$$S = \int_{-\pi}^{\pi} d\phi \int_0^1 dr D(r, \phi) \frac{\pi}{2} \sin\left(\frac{\pi}{2} r\right).$$

In examples, say D is a constant all retinal-surface points, and so is the same constant also in the transformed planar-polar picture. Then the correct integration yields $$S = 2\pi D \int_0^1 \frac{\pi}{2} \sin\left(\frac{\pi}{2} r\right) dr = 2\pi D,$$

which is correct, in being 2π steradians (for a full hemisphere) times the constant sensitivity. In embodiments, such estimates are reported in units of dB-steradians.

In another example of area-sensitivity integration, if there is a constant D(r, φ)=D but only over a small circle, origin-centered and of radius, for instance, r=½ in signature coordinates. The correct integral is πD/√2; indeed, the polar cap that comes down to polar angle π/4 does subtend exactly π/√2 steradians. However, there is a counter-intuitive aspect of such "cap" transformations: a circle-cap sitting on the original, physical retinal sphere is not generally a circle in the planar signature space. The example of a cap of radius r=½ does give a circular cap upon back-transformation, but that is because such a cap is pole-centered to begin with. The primary detail that is needed for circle-cap deformations is the angle formula:

$$\cos \Omega = \cos \theta \cos \theta_0 + \sin \theta \sin \theta_0 \cos(\phi - \phi_0),$$

expressing the exact subtended angle Ω between two spherical points (1, θ$_0$, φ$_0$) and (1, θ, φ). If (θ$_0$, φ$_0$) is the direction of the center of a circle-cap on the original sphere, then the signature-space substitution θ→πr/2 yields from the cos Ω formula an actual polar-coordinates equation for an (r, φ) path in signature space, and, unless θ$_0$=0, which is the special case of a pole-centered cap, a circle is not obtained in the signature plane, rather a kind of oval.

Figure 3:
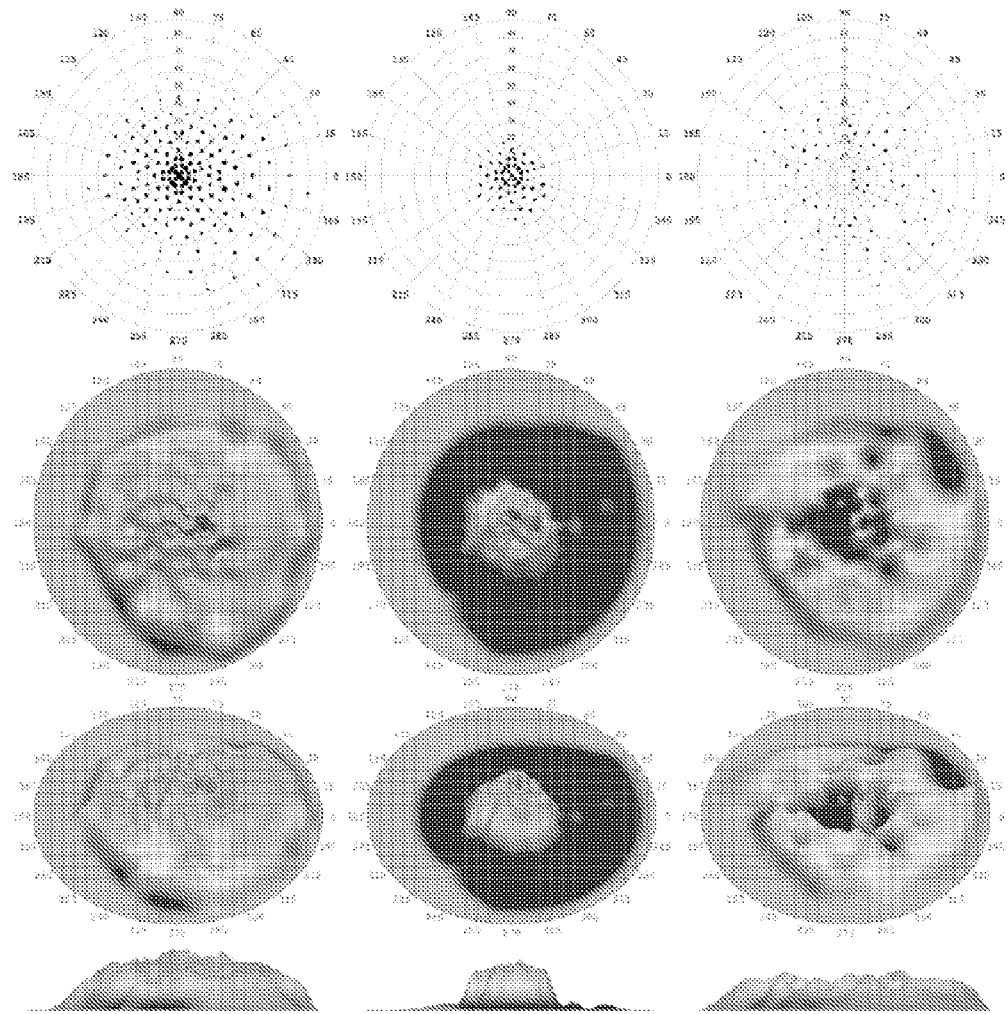
FIG. 3 illustrates a Hill-of-Vision (HOV) representation, in accordance with various embodiments. The data plotted in signature coordinates (upper three views) are, respectively left-to-right, from a normal subject (NO), a subject with retinitis pigmentosa (RP), and a subject with macular dystrophy (MD). A thin-plate spline (TPS) is used to infer a smooth surface (second row, left-to right for NO, RP, MD) as viewed from atop. The other variously tilted views are obtained via manual control in the VFMA application.

Referring to FIG. 3, in embodiments, the steps for visualization of the HOV, namely the sensitivity profile on the retina, may be as follows:

1. Load data points (anywhere from a few, to hundreds of such), as plotted in the upper strip of FIG. 3, the plotting being for two-dimensional signature space as previously defined. The three left-to-right plots are for NO (normal subject), RP, and MD (macular degeneration) subjects.
2. Interpret these discrete points as constraints on a spline surface, and show each such surface as in the second strip of FIG. 2, for instance, the thin-plate spline (TPS) described below.
3. As embodied in the VFMA application (below), allow for rotation/inspection of the spline surface, as in the remaining three-view strips of FIG. 3.

In embodiments, the black dots (data positions) each have respective data values. These may be seen as "spikes" coming out of the page, with heights given by dbm sensitivity measurement. Regardless of the nature of the spline, or the metaphor for imagining sensitivity values, the spline surface (for instance, the upper-right view of FIG. 2) is neither a picture of the retina nor a sensitivity map directly on the spherical retina; it is a picture of sensitivity in signature space, and may be warped somewhat by the Jacobian curvature to represent on-retina sensitivity. The three-dimensional spline at the upper-right of FIG. 2 shows a function defined on the unit disk in two-dimensions, and this is the basis for the signature calculations.

Some embodiments include the following task: given N input data vectors in D dimensions with given real evaluations, namely a set:

$$(\vec{r}_k = (r_{0,k} \ldots r_{D-1,k}) : k \in [0, N-1])$$

and an evaluation set:

$$(I(\vec{r}_k) : k \in [0, N-1]),$$

establish a smooth, real-valued spline function $S(\vec{r})$ such that for all $k \in [0, N-1]$ $$S(\vec{r}_k) = I(\vec{r}_k).$$

For instance, it is desirable to have a smooth function that agrees with I at each of the N input points.

An exemplary spline design runs as follows. Define a (nonnegative) radial-potential function $V(|\vec{r}|)$. For spline coherence (agreement on the input set) V diverges at $\vec{r} = \vec{0}$; however, in examples, V may simply be forced to be very large at said origin. Now a spline function S is defined on general D-dimensional vectors $\vec{t}$ by $$S(\vec{t}) := \frac{\sum_{k=0}^{N-1} V(|\vec{t} - \vec{r}_k|) I(\vec{r}_k)}{\sum_{k=0}^{N-1} V(|\vec{t} - \vec{r}_k|)}.$$

The way the potential works is, for vector $\vec{t}$ coinciding with an input vector $r_k$, it is expected that, due to the divergence of $V(0)$, the surviving term in the ratio of sums above is just $I(\vec{r}_k)$.

In examples, a computationally practical choice for the potential function is $$V(R) = \frac{e^{-LR}}{(R^2 + \epsilon)^{\alpha}},$$

where $\epsilon$ is very small. When $\alpha := \frac{1}{2}$, $\epsilon := 0$ which is the radial Yukawa potential of nuclear physics. Thus potentials of this exponential form are referred to as "Yukawa-class" potentials herein, and freedom of choice is presumed for L, $\epsilon$, $\alpha$.

FIG. 4 shows choices of parameters for the potential V and the resulting spline surfaces. In each case the input data are two-dimensional evaluations, and so have $D = 2,$ $N := 21,$ $$\{\{\vec{r}_0, I(\vec{r}_0)\}, \{\vec{r}_2, I(\vec{r}_2)\}, \ldots, \{\vec{r}_{20}, I(\vec{r}_{20})\}\} = \begin{pmatrix} 1 & 0 & 0 \\ \cos(\frac{\pi}{8}) & \sin(\frac{\pi}{8}) & 0 \\ \frac{1}{\sqrt{2}} & \frac{1}{\sqrt{2}} & 0 \\ \cos(\frac{3\pi}{8}) & \sin(\frac{3\pi}{8}) & 0 \\ 0 & 1 & 0 \\ \cos(\frac{5\pi}{8}) & \sin(\frac{5\pi}{8}) & 0 \\ -\frac{1}{\sqrt{2}} & \frac{1}{\sqrt{2}} & 0 \\ \cos(\frac{7\pi}{8}) & \sin(\frac{7\pi}{8}) & 0 \\ -1 & 0 & 0 \\ \cos(\frac{9\pi}{8}) & \sin(\frac{9\pi}{8}) & 0 \\ -\frac{1}{\sqrt{2}} & -\frac{1}{\sqrt{2}} & 0 \\ \cos(\frac{11\pi}{8}) & \sin(\frac{11\pi}{8}) & 0 \\ 0 & -1 & 0 \\ \cos(\frac{13\pi}{8}) & \sin(\frac{13\pi}{8}) & 0 \\ \frac{1}{\sqrt{2}} & -\frac{1}{\sqrt{2}} & 0 \\ \cos(\frac{15\pi}{8}) & \sin(\frac{15\pi}{8}) & 0 \\ 1 & 0 & 0 \\ \frac{1}{2} & 0 & 1 \\ 0 & \frac{1}{2} & 4 \\ -\frac{1}{2} & 0 & 3 \\ 0 & -\frac{1}{2} & 2 \end{pmatrix}$$

Thus, for example, the very last array entry, namely $\{0, -\frac{1}{2}, 2\}$, means that the value of the I-function at $(x, y) = (0, -\frac{1}{2})$ is 2. In fact, the input data above has exactly four points with nonzero evaluations (1, 2, 3, 4) in the indicated order. However, a necklace of points has been intentionally placed around the unit circle, all having the value 0, to force in this particular demonstration the boundary condition that the spline wants to vanish on the unit circle. Other boundary conditions may just as easily be specified by throwing appropriate input data into the set.

Another spline technique is thin plate splines (TPS). In embodiments, thin plate spline smoothing is inspired by the modeling of thin metal plates in elasticity theory. FIGS. 2-5 show the TPS in action. In various embodiments, just as with the nuclear spline design, the TPS has extra input; namely, the retinal-sensitivity data, and a necklace of zeros, to force near-vanishing of the TPS at the circle's edge.

In one example, a first method for generating a two-dimensional signature for a spline surface is to create a nonlinear-Mercator projection. This refers to the classical Mercator map projection, except the lines of "latitude" are nonlinearly warped so that every sector has equal area. Then, a Mercator plot may be vertically integrated to yield a rotationally invariant one-dimensional signature, or "strip-chart." Another signature may involve taking the two-dimensional FFT of the aforementioned nonlinear-Mercator two-dimensional signature.

One reason to create a spline surface is to be able to invoke numerical integration algorithms on discrete data sets. In one example, a general expansion for splined unit-circle data (radial coordinates (r, φ) and a spline function S(r, φ) is the Bessel expansion valid for cases where S vanishes on the unit circle:

$$S(r, \phi) = \sum_{m=-\infty}^{\infty} \sum_{k=1}^{\infty} s_{mk} J_m(rz_{mk}) e^{im\phi}.$$

Here, $z_{mk}$ denotes the k-th positive zero of the Bessel function $J_m$. For real-valued splines S, negative m may be avoided by noting $J_m = (-1)^m J_{-m}$ and observing cos φ, sin φ terms. The formal inversion that yields the actual coefficients ($s_{nk}$) is $$s_{nk} = \frac{1}{\pi} \frac{1}{(J'_n(z_{nk}))^2} \int_0^{2\pi} d\phi \int_0^1 r \, dr S(r, \phi) J_n(rz_{nk}) e^{-in\phi}.$$

The strategy, then, to provide a "signature" as a set of expansion coefficients ($s_{nk}$) for a discrete data input set may be:

(1) Create a spline S from the input data, making sure to use a "necklace" of zero-points around the unit circle so that S itself vanishes or nearly so on the unit rim;

(2) Choose a cutoff parameter M such that coefficient ($s_{nk}$) indices will run over n∈[−M, M], k∈[1, M], for instance; again, converting to pure-real algebra may allow n to be only in [0, M];

(3) Perform numerical integration to obtain the M(2M+1)= $O(M^2)$ coefficients ($s_{nk}$);

(4) Check that the spline surface reconstructs well via the (now finite) Bessel sum; and (5) Report the signature of the original data as the set ($|s_{nk}|^2$).

In embodiments, the signature elements $|s_{nk}|^2$ amount to a kind of power spectrum under Bessel decomposition. In general, all rotations of some data set in the unit circle should exhibit equivalent signatures, and this should be tested.

A fourth exemplary signature may be referred to as a "fractal signature," although perhaps more accurate would be "fluctuation signature." The concept arises in computer graphics; namely, a lunar landscape, for instance, of dimension near three is jagged, e.g., attempting to be space-filling. On the other hand, a smoothly undulating lowlands, like an almost flat meadow, will have dimension closer to two. The fractal measure uses the standard box-dimension counting from computational physics, in order to assess the approximate fractal dimension of the spline surface.

Figure 10:
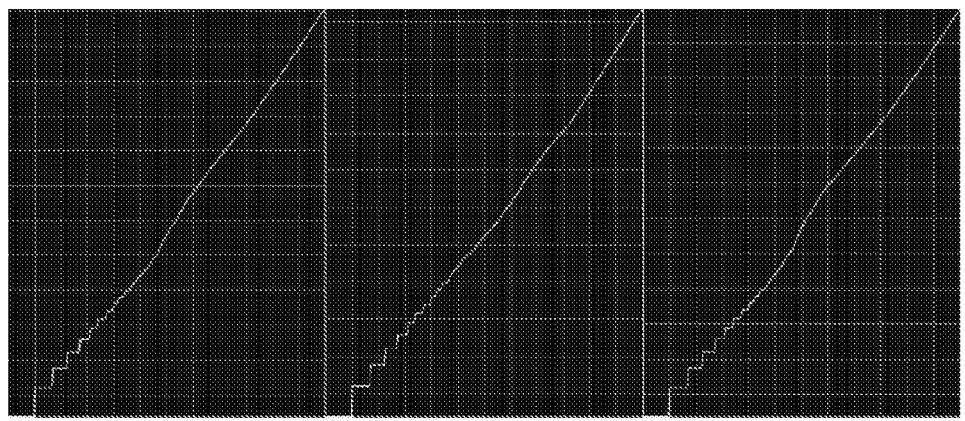
FIG. 10 illustrates Fractal-signature results for NO, RP, and MD subjects, left-to-right respectively, in accordance with various embodiments. Though these plots look very similar, the dimension Δ varies subtly; however, there does appear to be a systematic trend over normal vs. diseased subjects. The actual dimensions, left-to-right, are Δ=2.63, 2.58, 2.53.
Figure 11:
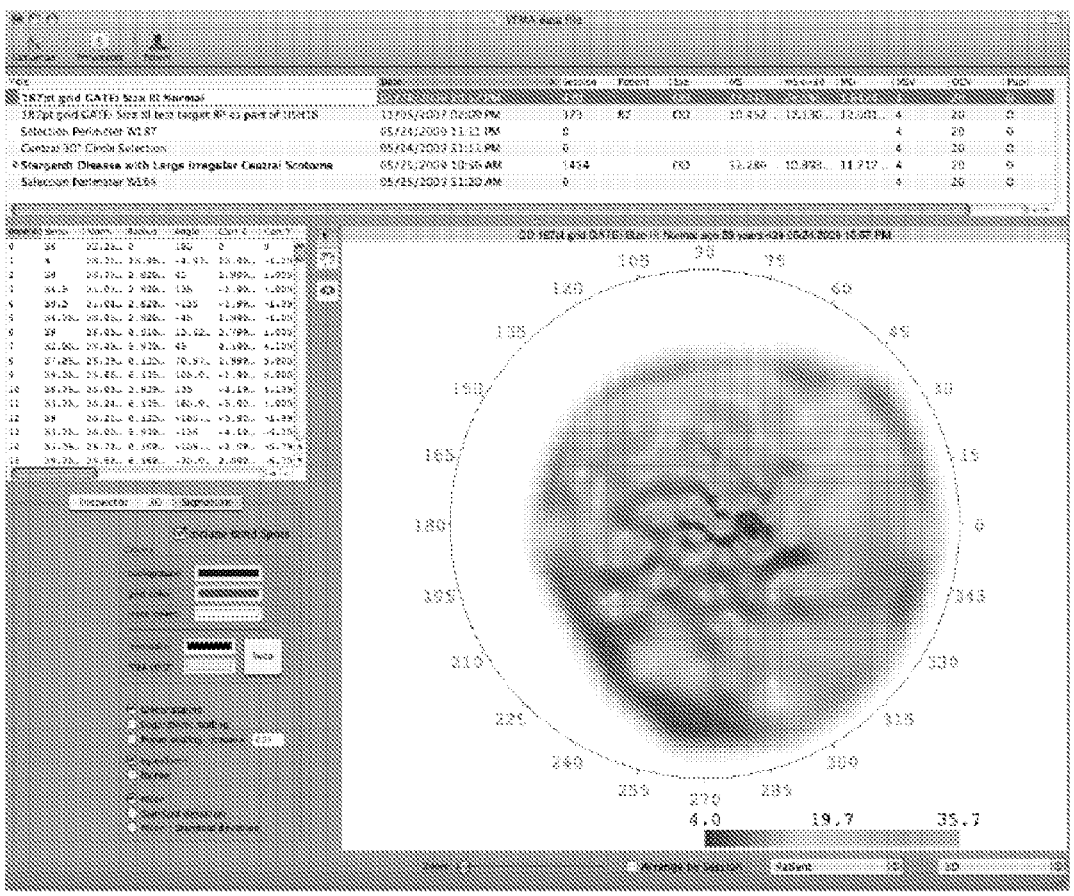
FIG. 11 illustrates a typical appearance of the HOV within the VFMA application, in accordance with various embodiments.
Figure 12:
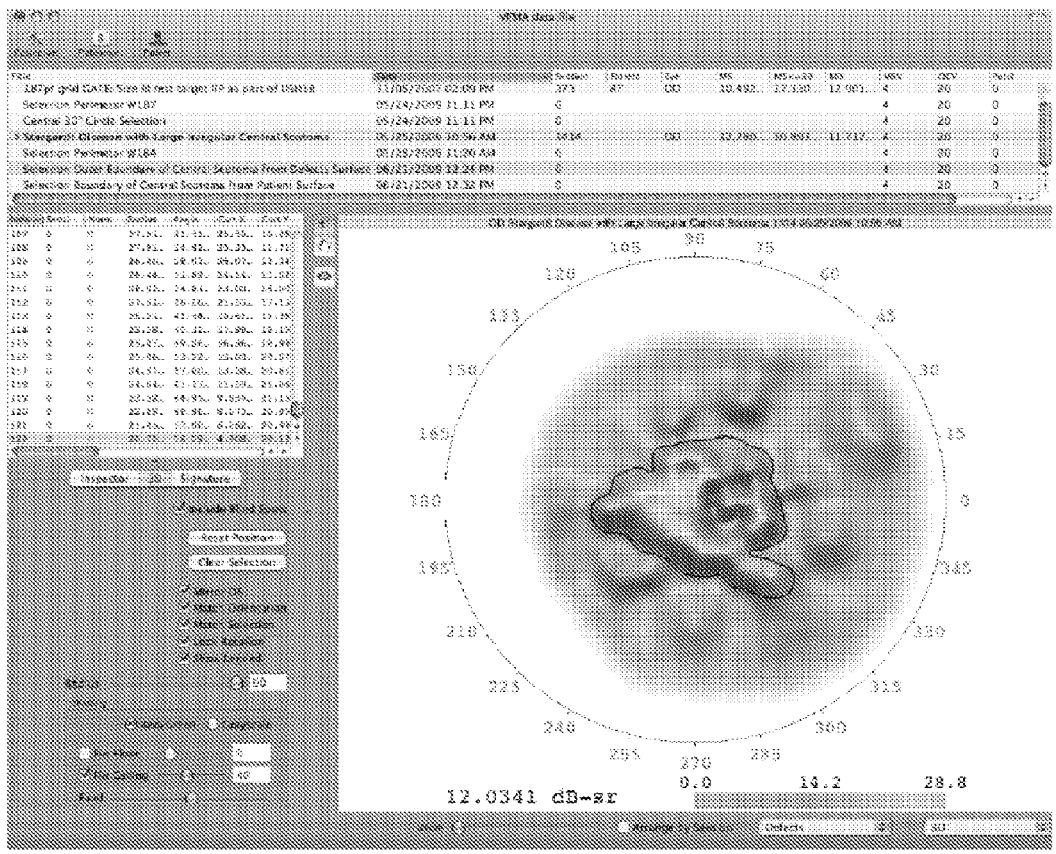
FIG. 12 illustrates how the VFMA application also allows "scribing" of specific areas of the HOV either as remaining sensitivity or as a scotoma or defect within the HOV. In this instance, a "Defects" model was created by subtraction of the HOV for subject MD from FIG. 2 from the HOV of an age-adjusted normal subject. Outlining the base of the inverted scotoma in this "Defects" space allows the measurement of the volume of the scotoma, which is reported as 12.03 dB-steradians.

Referring to FIG. 10, the plot may have, for three-dimensional boxes of side ε, a horizontal axis log(1/ε), and a vertical axis #(ε), the latter being the number of ε-boxes that contain spline points. For this fractal measurement, the spline is used on a 256×256 grid, so there are 216 points that can occupy boxes.

Figure 6:
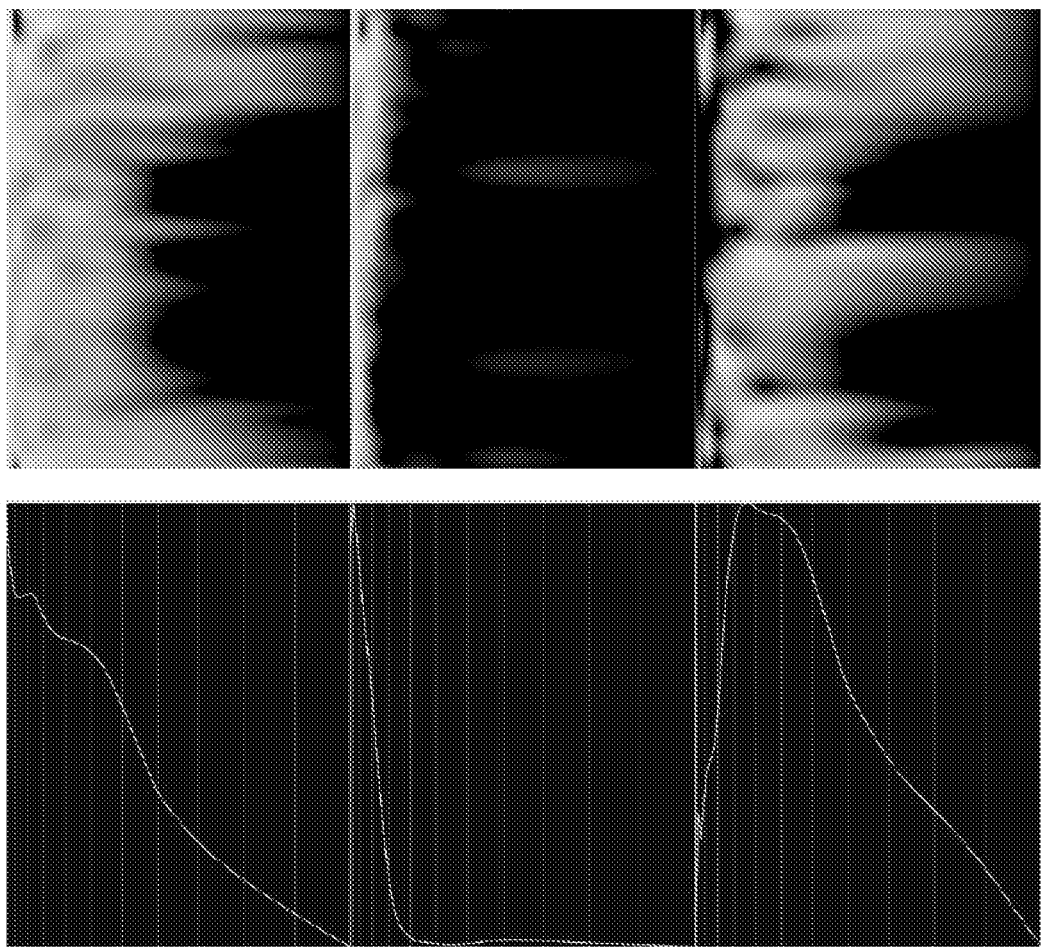
FIG. 6 illustrates Mercator-signature results for NO, RP, MD subjects, left-to-right respectively, in accordance with various embodiments. The maximum amplitudes of the normalized signature curves are, from left-to-right respectively, 30.0, 22.3, 13.0. The signature plots are created via columnar summation of the upper, two-dimensional Mercator plots.
Figure 7:
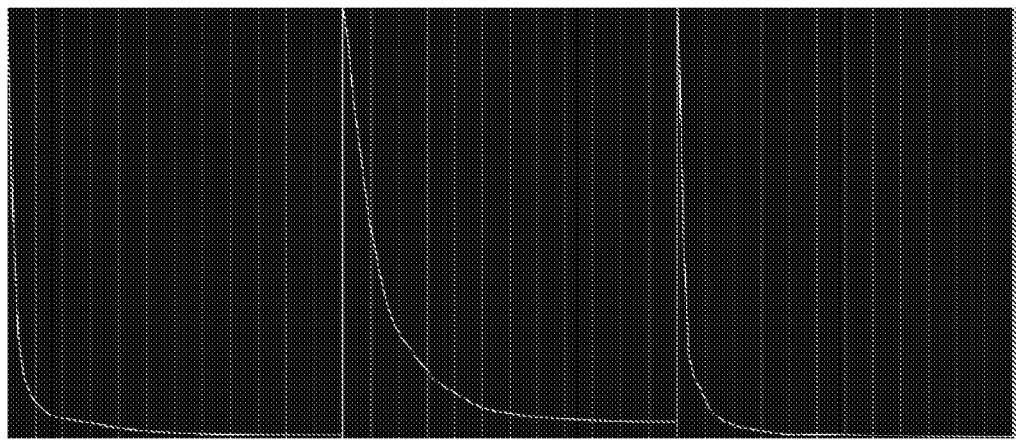
FIG. 7 illustrates Radial-Fourier signatures for NO, RP, and MD subjects, left-to-right respectively, in accordance with various embodiments. The signature curves are created via columnar summation of the relevant two-dimensional power-spectrum plot. These are normalized signatures; the actual signature maxima are, for NO, RP, MD respectively, 4340, 743, 3163; therefore the normal subject (left-most panel) has the largest signature excursion.
Figure 8:
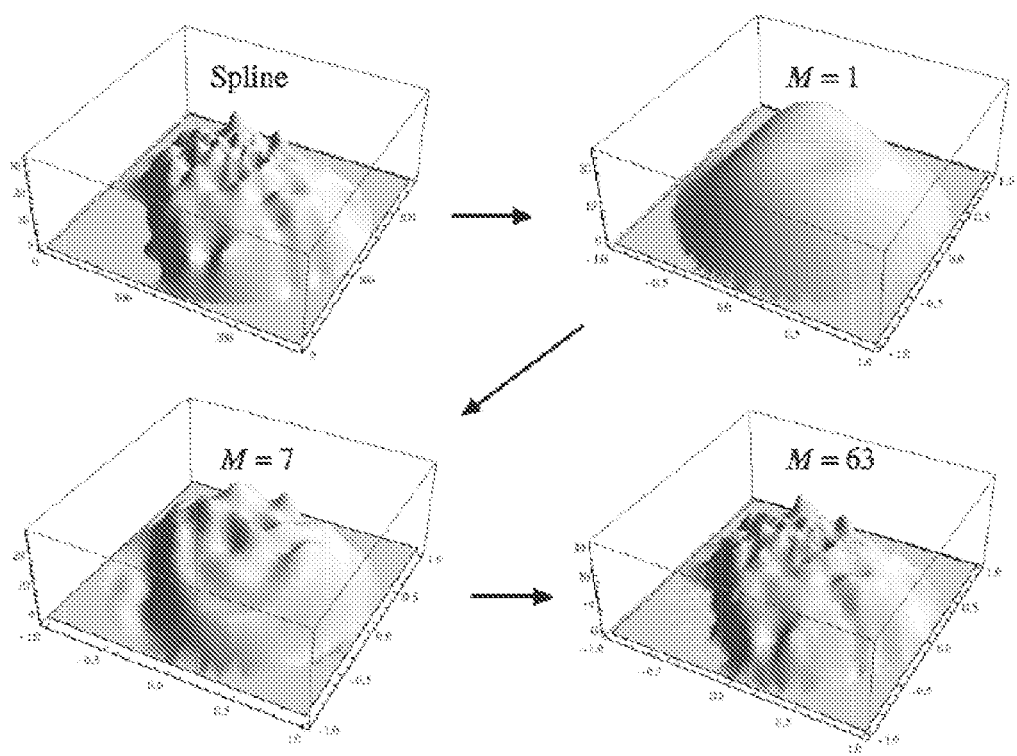
FIG. 8 illustrates how, in the Bessel-signature strategy, splined retinal data in signature space (upper-left view) is broken down into (2M+1) Bessel functions, in accordance with various embodiments. For M=1 (upper-right view) the Bessel functions add to a shape only vaguely reminiscent of the original spline. The sum of the relevant 15 Bessel terms for M=7 (lower-left view) still yields insufficient resolution, but for M=63, the sum of the 127 Bessel terms can be seen (lower-right view) to be in excellent agreement with the original spline. The whole strategy is based on the idea that the coefficients in the Bessel superpositions are themselves the "Bessel signature" for the given retina.

In some embodiments, for the Mercator signature, normal (NO) eyes tend to give essentially linear-descending ramps, while diseased eyes tend to be very different. See e.g., FIG. 6. By contrast, in embodiments, for the Fourier signature, normal (NO) eyes tend to have exponentially decaying appearance, as do macular dystrophy (MD) eyes. However, the maximum amplitude for MD is reduced. See, e.g., FIG. 7.

Figure 9:
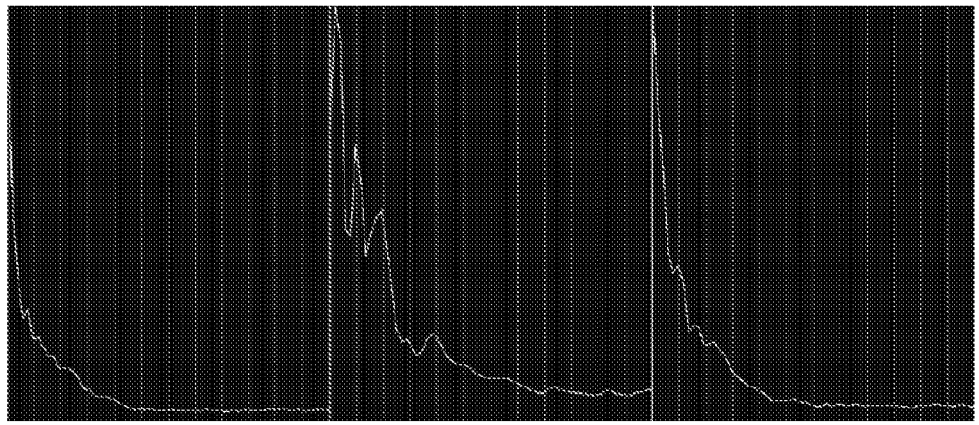
FIG. 9 illustrates Bessel-signature results for NO, RP, and MD subjects, left-to-right respectively, in accordance with various embodiments. These signatures are obtained by columnar summation of log $|s_{jk}|$ from the relevant two-dimensional Bessel-coefficient matrix. Again, these signatures are visually normalized, the actual respective maxima being: 0.81, 0.23, 0.58.

In various embodiments, for the Bessel signature, NO eyes typically exhibit a damped form, as do MD eyes; yet again, the diseased case has smaller maximum amplitude. See, e.g., FIG. 9. An exemplary Bessel signature that is a pure spike (technically, a delta-function at far left) would mean that the HOV is actually the zeroth-order Bessel function $aJ_0(br)$ for some constants a, b. That this is never experimentally the case indicates that in normal (NO) situations, a certain fluctuation in the HOV is expected.

In some embodiments, for the fractal signature (see, e.g., FIG. 10) there is no visually obvious difference between normal and diseased eyes. However, normal (NO) situations tend to have highest fractal dimension Δ. Moreover, as subtle as Δ turns out to be experimentally, the Δ values may be sorted by disease, yielding an important diagnostic measure. In embodiments, the normal retina is non-smooth in a quantifiable sense.

In various embodiments, VFMA serves as a platform for the design and testing of algorithms to generate three-dimensional models of the HOV for the entire field of vision of the human eye, as measured clinically using static perimetry. VFMA also is useful for quantification and analysis of the visual field for clinical diagnosis, characterization of the nature and extent of the field defects, and for monitoring the natural history of field loss in health and disease. This platform also enabled the development and evaluation of mathematical signatures based on Radial Fourier, Bessel, and Fractal analyses of the surface of the Hill of Vision to further characterize the field loss.

In embodiments, threshold values from the perimeter are imported into the application and converted to differential luminous sensitivity (DLS) values. In some embodiments, the main window of the application has a rectangular window spanning its width superiorly where the files of data for each eye are displayed, along with the title of the file, the test date, session, patient number, eye, mean sensitivity (total), mean sensitivity ≤30°, mean defect, MSV (minimal sensitivity value), OCV (Octopus conversion value), and pupil size. In embodiments, selecting one or more of the test data sets allows the operation of other functions that display the test points for the entire grid (with the points equal size or scaled by sensitivity), the three-dimensional model of the DLS values fit with an infinitely differentiable elastic thin plate spline, the normal three-dimensional model of the HOV for the age of the subject, and the defect surface, which is the three-dimensional model of the normal HOV from which the subject's data has been subtracted. In some embodiments, the spline is an infinitely differentiable spline that is not constrained by any interval between grids or any orientation of grids, e.g., the spline can handle any amount of data input and any interval distance or orientation of points. In other embodiments, another menu allows display of the HOV by a Mercator projection map and signature graphs of the Mercator function and Radial Fourier spectrum (by column and row), the Bessel function, and the Fractal analysis.

In other embodiments, other menus allow creation of selection templates for measuring the volume in decibel-steradians (dB-steradians) of the entire HOV as assessed by the grid pattern and distribution, selections based on circles of specific diameters (which can be moved eccentrically on the nonlinear-Mercator polar projection to measure a circular representation of the HOV other than centered on the pole), and for selections of scotomas that can be anywhere in the field and different for each eye. All of these selections may be stored for future use, in certain embodiments, for measurements of other field data.

Figure 13:
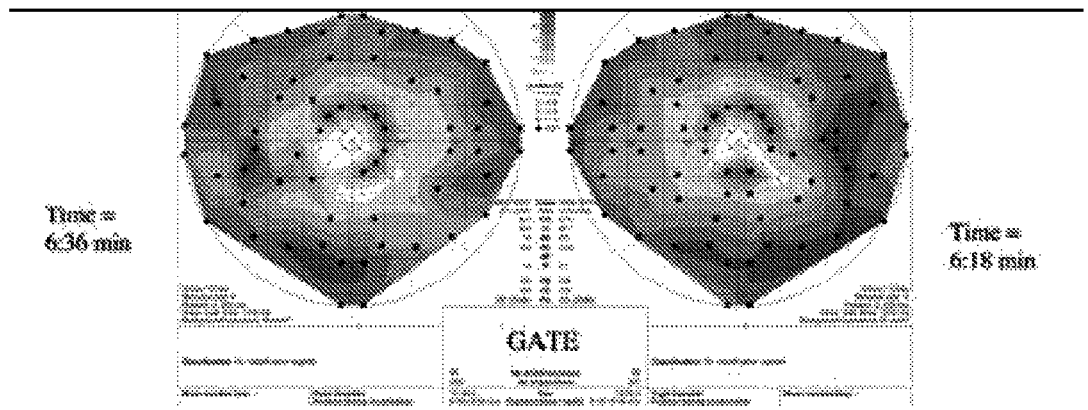
FIG. 13 shows a comparison of visual field evaluations for a subject with retinitis pigmentosa (RP) using the Humphrey full-threshold 30-2 test (HFA, top) and the German Adaptive Threshold Estimation (GATE) strategy (bottom), in accordance with various embodiments.

One exemplary embodiment is shown in FIG. 13, which illustrates a comparison of visual field evaluations for a subject with retinitis pigmentosa using the Humphrey full-threshold 30-2 test (HFA, top) and the German Adaptive Threshold Estimation (GATE) strategy (bottom) in accordance with various embodiments. This figure shows the superior performance of earlier 30-degree grid patterns with the GATE strategy over the Humphrey full threshold (HFA) 30-2. The top two grayscale plots show the visual fields of a subject with retinitis pigmentosa as part of Usher syndrome evaluated with the Humphrey 30-2 test. The bottom fields are of the same subject using the GATE strategy with the earlier designed grid. The time required for the GATE strategy was 6:36 minutes OD and 6:18 minutes OS: about a third of the time required for the less sensitive HFA 30-2. The central partial ring of depressed field represented by the arrow, which correlated with RPE depigmentation on fundus photography, was not detected by the HFA 30-2 but was with the GATE strategy 30-A grid. Over 30 grids to test the peripheral visual field were designed, and six were chosen for further study. The first grid was designed for testing the full-field in subjects with retinitis pigmentosa. Using the GATE strategy, this grid tests the entire field from 80 degrees temporally to 56 degrees nasally in the same time required with the Humphrey instrument, using the 4-2-1 strategy, to test only the central 30 degrees. Although this field tests the entire visual field, in order to further reduce the time required for testing, more efficient grids with fewer points may be utilized to improve the speed of testing.

Figure 14:
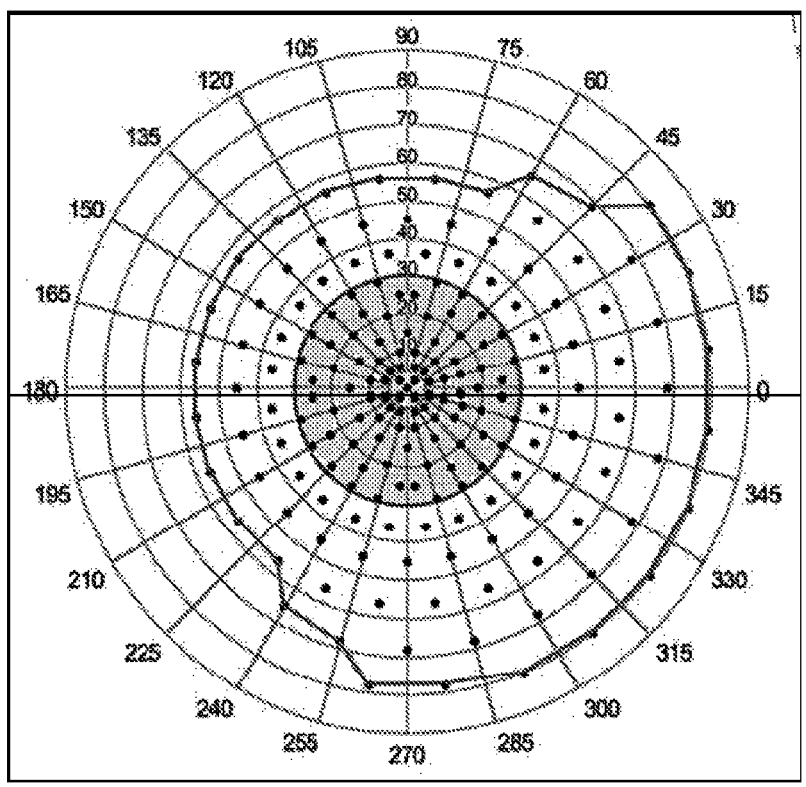
FIG. 14 shows a grid ("W7") of test sites for use with the GATE strategy for testing the entire visual field of subjects with RP and allied disorders, in accordance with various embodiments.

In another exemplary embodiment, FIG. 14 shows a grid ("W7") of test sites for use with the GATE strategy for testing the entire visual field of subjects with retinitis pigmentosa and allied disorders in accordance with various embodiments. This test grid, called W187 or simply W7, is composed of 187 test points and with the GATE strategy takes from 13 to 20 minutes per eye to test the entire field. The result, which takes equal or less time than the full-threshold test, is retinal sensitivity data for an area six times that of the Humphrey 30-2 test grid, which tests only the central 30 degrees. Evaluation of static perimetry was performed with the W7 grid and the GATE strategy in conjunction with kinetic perimetry using Semi-automated Kinetic Perimetry (SKP) in subjects with RP and related disorders. Photoreceptor disease, such as occurs in subjects with retinitis pigmentosa and related disorders, results in greater loss of retina sensitivity to targets presented in a static or non-moving fashion than to targets present as a kinetic or moving test target. This phenomenon is known as statokinetic dissociation and its basis is the reason why subjects with retinitis pigmentosa often have greater difficulty seeing stationary targets. The Octopus 101 static perimeter (Haag-Streit) may be used as the visual field instrument for both static and kinetic visual field testing. The types of data obtained with this instrument include the kinetic visual field and the GATE static visual fields.

Figure 15:
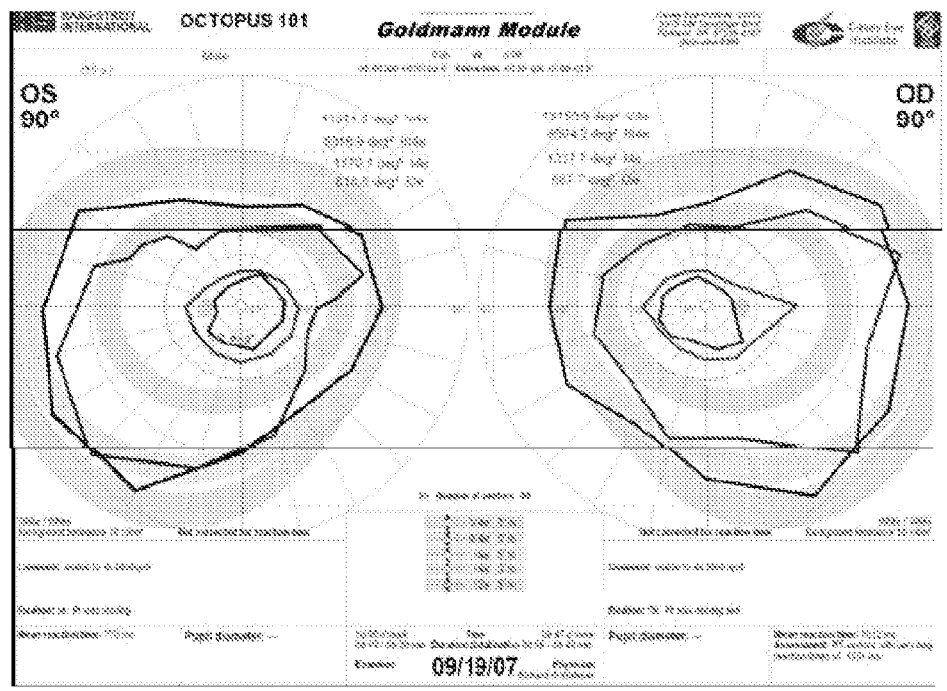
FIG. 15 shows the kinetic visual field of a 10-year-old child with type I Usher syndrome from mutations of the gene, MYO7A, for myosin VIIA, the most common form of type I Usher syndrome, in accordance with various embodiments.

Another exemplary embodiment is shown in FIG. 15, which illustrates the kinetic visual field of a 10-year-old child with type I Usher syndrome from mutations of the gene, MYO7A, for myosin VIIA, the most common form of type I Usher syndrome. This view shows a broad band denoting the normal range in which the target should be seen. Note that the largest, brightest test target, V4e, was seen just central to, or in some instances just within, the normal zone, indicating relatively good perception of the moving target for this test size. On the other hand, the smaller I4e and smaller and dimmer I2e test targets had to be brought considerably closer to fixation to be seen, indicating that the retina is much less sensitive than normal to smaller and dimmer test targets than larger and brighter targets. This type of visual field testing is easily understood by subjects but the findings are harder to analyze statistically to follow for stability or progression.

Figure 16:
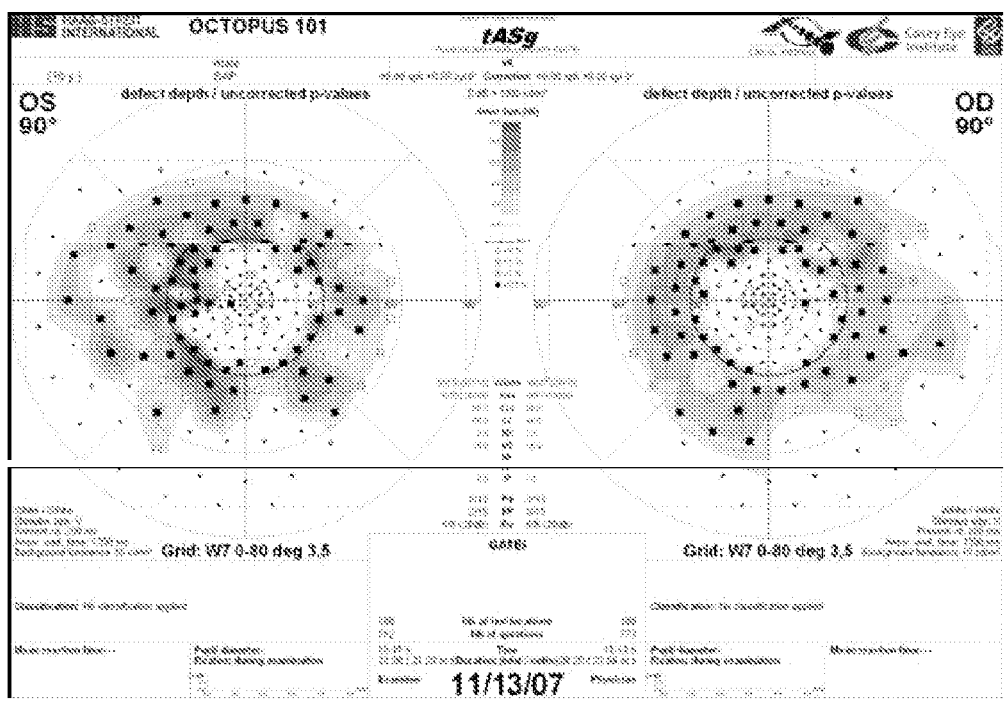
FIG. 16 shows a static perimetry visual field using the GATE strategy and the W7 grid of the 10-year-old child with type I Usher syndrome represented in FIG. 15, in accordance with various embodiments.

FIG. 16 shows a static perimetry visual field using the GATE strategy and the W7 grid of the 10-year-old child with type I Usher syndrome represented in FIG. 15, in accordance with various embodiments. White indicates normal retinal sensitivity whereas varying shades of gray indicate decreased retinal sensitivity. Using the largest, brightest test target, the sensitivity is reasonably good centrally but is reduced in a patchy nature scattered throughout the midperiphery. This highly nuanced information can only be obtained with static perimetry. For each of the 187 test sites, a numeric sensitivity level is obtained, which may be used for digital modeling of the defects as well as for developing parameters to follow in clinical trials.

In particular examples, the largest grid has 187 test sites. However, in some embodiments, smaller grids with 175, 158, 143, 124, and 101 test sites were also designed and tested. All of these grids have value for specific purposes, both in the clinic and in research. Mathematical modeling of the HOV and determination of visual field defects using threshold and/or corrected sensitivity values obtained with the W187 grid and the GATE strategy may be used to improve the diagnosis and develop endpoints for monitoring patients in clinical trials.

In addition, as described above, the data may be transformed in some embodiments, using mathematical signature analysis, according to various embodiments. For example, in embodiments, the Mercator projection may provide information on the distribution of sensitivity by polar direction and distance, whereas the Radial Fourier analysis may provide information on the magnitude and spectrum of spatial frequencies. In other embodiments, analysis by Bessel function may provide a first look at how the visual field can undergo decomposition according to combinations of mathematically defined shapes. In certain embodiments, of these three signatures, the Mercator may provide the most readily understandable information. However, in embodiments, additional signatures and mathematical analyses, including fractals, may be used to provide additional information about the visual field of the normal and diseased eye.

Figure 17A:
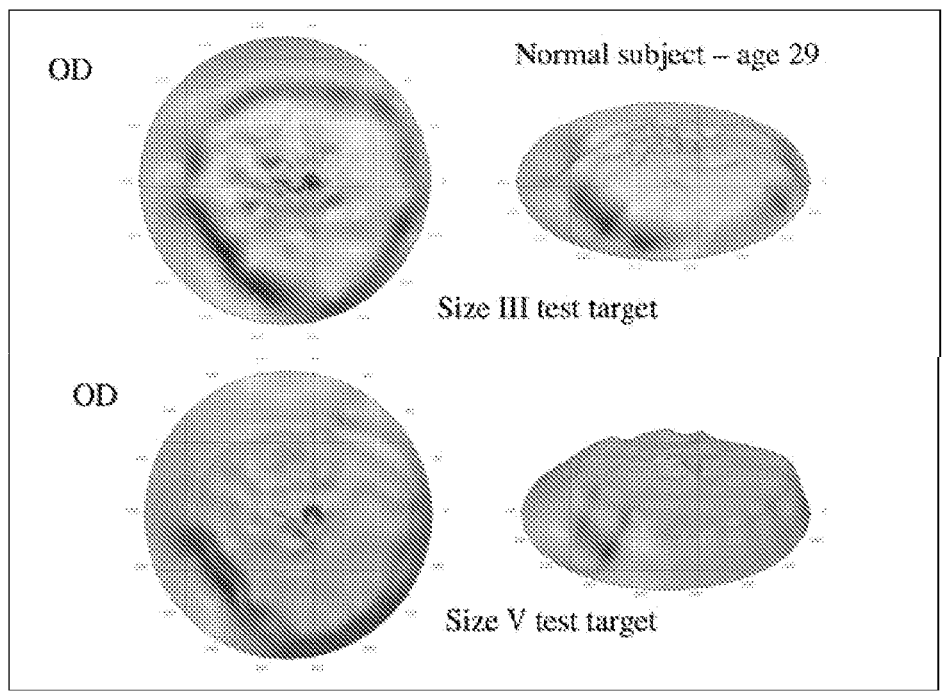
FIG. 17A shows the Hill of Vision (HOV) in a normal subject using the W187 grid and size III and V test targets.

In an example, FIG. 17A shows the HOV in a normal subject using the W187 grid and size III and V test targets in accordance with various embodiments. The three-dimensional HOV for a young subject with normal vision is shown to the right in a polar view on the left and a side view on the right. Right and left eye sensitivities were averaged and presented as a left eye for a size III test target (0.43 degree diameter) above and a size V test target (1.7 degree diameter) below. The height of the hill reflects the sensitivity. The gradations at the inferonasal edge of the field on the right reflect degrees of loss of sensitivity from the shadow of the nose. Note that greater sensitivity, particular in the periphery, for the size V test target. This greater sensitivity with the size V test target is achieved without any loss of resolution at the higher end, e.g., no "ceiling effect," and represents an average increase in the "effective dynamic range" of 5 dB centrally and 8 to 10 dB peripherally.

Figure 17B:
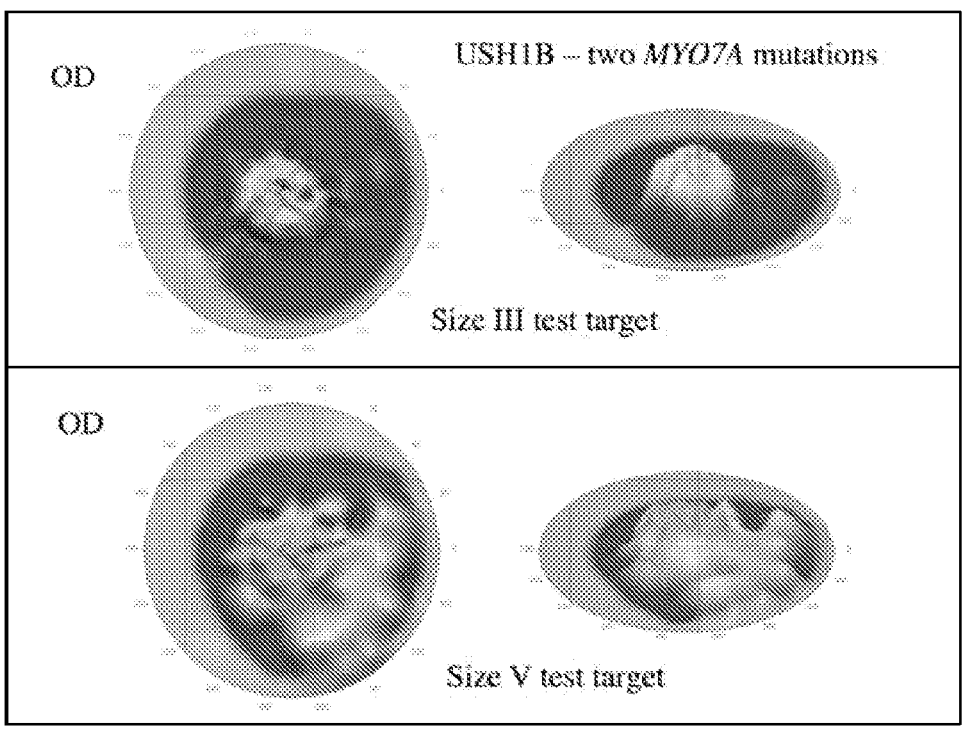
FIG. 17B shows the HOV for a 10-year-old child with Type I Usher syndrome from two MYO7A mutations using the W187 grid and sizes III and V test targets.

In another example, FIG. 17B shows the HOV for a 10-year-old child with Type I Usher syndrome from mutations of MYO7A, the gene for myosin-7A, using the W187 grid and sizes III and V test targets in accordance with various embodiments. This view shows the three-dimensional HOV for the right eye of the subject with Usher syndrome shown in FIGS. 15 and 16. The surface of the HOV is less elevated than normal and, for the size III test target, is discernible only in the center portion of the test field. With the size V test target, there is much more sensitivity but it is very irregular, reflecting localized regions of greater or lesser disease of the retina. Thus, the size V test target provides more indication of remaining vision than does the size III test target without loss of resolution at the higher sensitivities. Thus, the size V test target is much more appropriate for testing subjects with retinitis pigmentosa and allied disorders with significant sensitivity losses.

Figure 18:
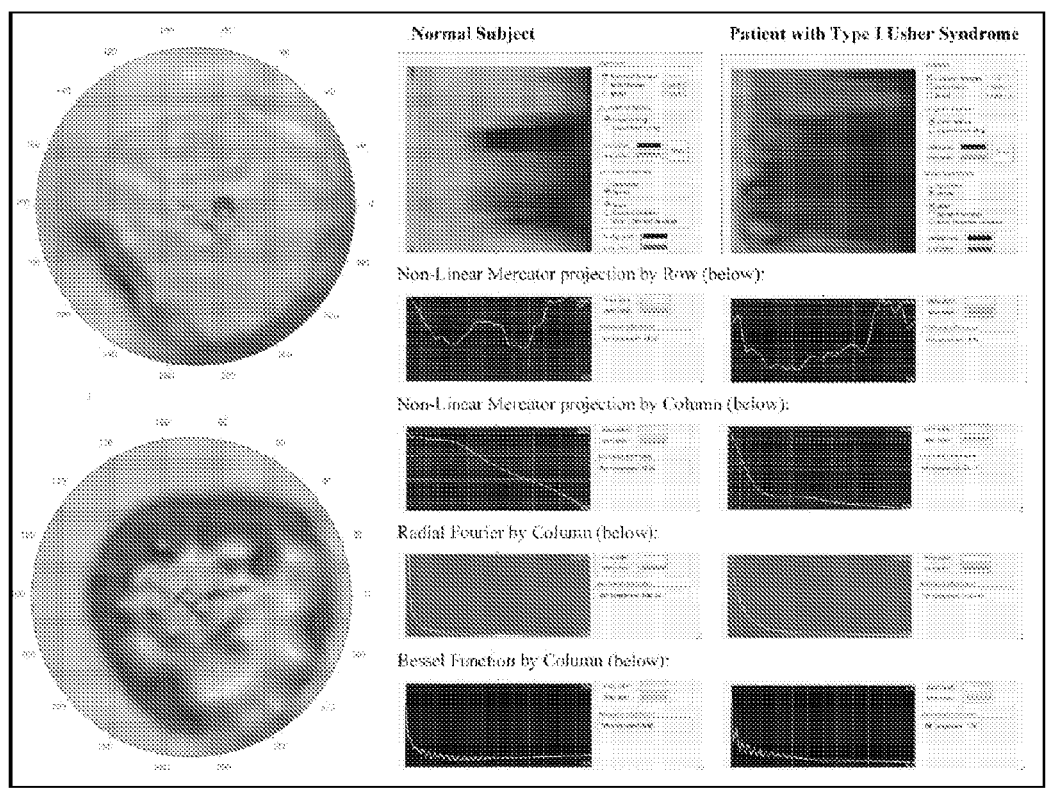
FIG. 18 shows Mercator projections (top graphs) quantifying loss of vision and signatures (two lowest graphs) of the field using the size V test target of the normal subject shown in FIG. 17A (below, left) and the right eye of the subject with Usher syndrome who had two mutations of MYO7A (below, right) shown in FIG. 17B, in accordance with embodiments.

FIG. 18 shows an example in which Mercator projections (top graphs) quantify loss of vision and signatures (two lowest graphs) of the field in accordance with embodiments, using the size V test target of the normal subject shown in FIG. 17A (below, left) and the right eye of the subject with Usher syndrome who had two mutations of MYO7A (below, right) shown in FIG. 17B. The Mercator map of the visual field may quantify the loss of vision by region. The center of the visual field is to the far left of the top graphs and the periphery is to the right. The degree of sensitivity at each polar direction, from 0 to 360 degrees, is depicted. The two graphs just below the Mercator projection are line graphs of the sensitivity by row and column. For the subject with RP, the visual sensitivity is considerably less but also in a different distribution compared to the normal subject.

Figure 19A:
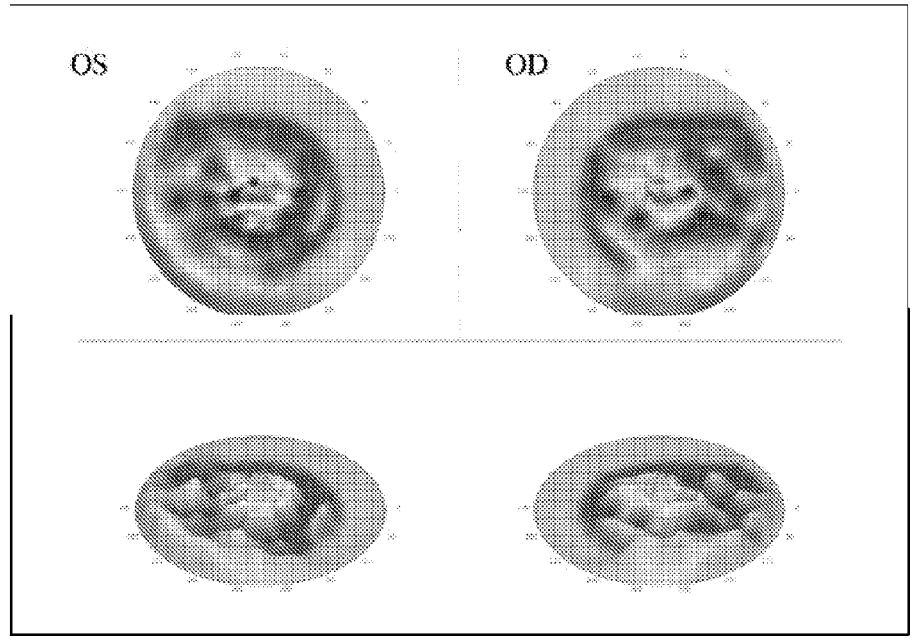
FIGS. 19A and 19B are panels illustrating plots of the HOV for two subjects with Usher syndrome, in accordance with embodiments.

FIG. 19A shows exemplary three-dimensional plots of the HOV for a 9-year-old subject with Usher Syndrome Type I. The subject had only one mutation of MYO7A of uncertain significance; molecular testing was inconclusive because only one sequence change of uncertain significance was found. The three-dimensional plots bear striking resemblance to those of the previous subject who had a firm molecular diagnosis of Usher Type I from mutation of MYO7A.

Figure 19B:
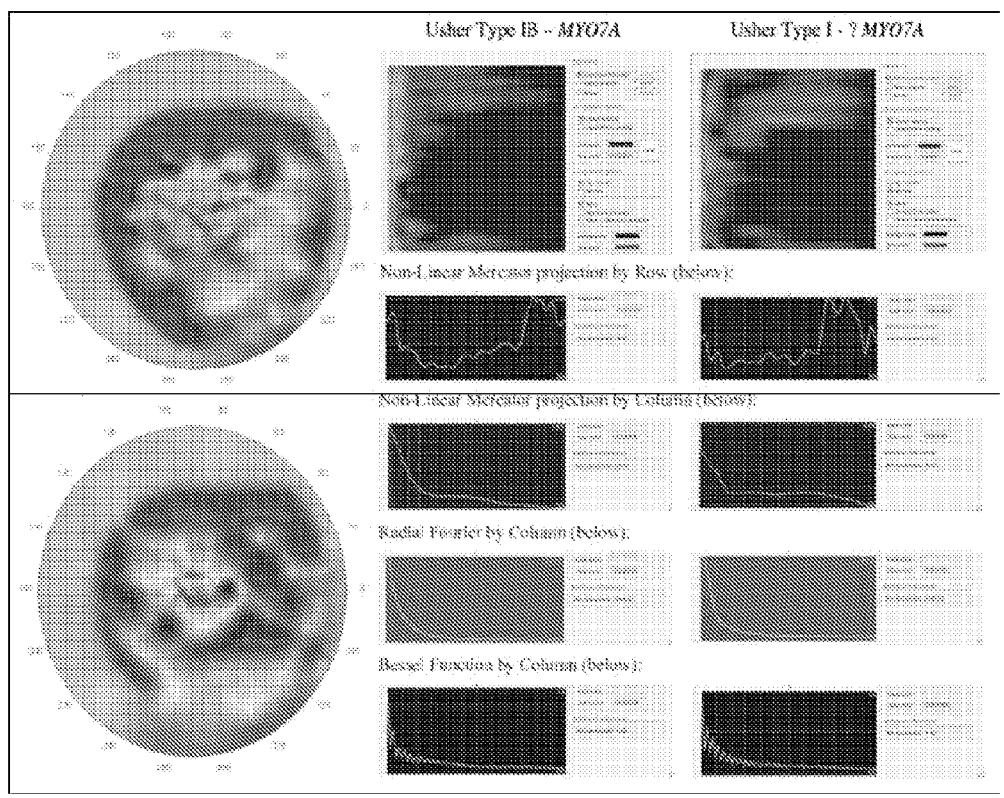

FIG. 19B shows exemplary three-dimensional plots (left), Mercator projections (top graphs) and signatures (two lowest graphs) of the fields of vision in accordance with various embodiments, using the size V test target of the subject with Usher syndrome shown in FIGS. 15B and 18 (upper left) and the right eye of the subject shown in FIG. 19A. The Mercator map of the visual field quantifies the loss of vision by region. The center of the visual field is to the far left of the top graphs and the periphery is to the right. The degree of sensitivity at each polar direction, from 0 to 360 degrees, is depicted in the amount of shading from left to right starting at the bottom and going up. The two graphs just below the Mercator projection are line graphs of the sensitivity by row and column. For the subjects with RP, the visual sensitivity is considerably less than normal, but similar in appearance for the two subjects. The mathematical signatures for the Mercator projection and the mathematical signatures for the Radial Fourier and Bessel function are nearly identical, providing evidence that the patterns of field losses are the same. This similarity of field defects supports the likelihood that the subject with only one sequence change in MYO7A represents myosin-7A related disease.

In embodiments, additional signatures and global and regional measures of sensitivity and field loss may be provided, as discussed above. Additional analytic signatures for the HOV, e.g., Fractals and Wavelets, may be provided. In addition, in embodiments, implementation of measurement of parameters of global and local damage to the visual fields may be provided. These include the Mean Sensitivity (MS), both within the central 30 degrees and for the entire field, the Mean Defect (MD), and the Loss Variance (LV). The MS and MD are global indices of differential luminance sensitivity and mean loss or defect compared to a group of age related normal subjects, respectively. Also, two different scales of luminance sensitivity exist, one for the Octopus perimeters and a second scale for the Humphrey perimeters. Thus, to compare these two scales, adjustments may be made. Since the Mean Defect compares the subject's data to age-related normal subjects, the MD is independent of whether it was determined using a Humphrey or an Octopus instrument. Since the full-field grids test points that are well beyond the central 30 degree region, in order to calculate the MD, normal values may be collected for both the size III and the size V test targets for all new test sites not part of smaller grids. Fitting of this data to a spline may allow extrapolation of normal sensitivity values for points not represented in the original data.

In embodiments, determination of value of three-dimensional plots and mathematical signatures to predict disease type at the cellular level and at the molecular level may be provided. The correlation of the plots and signatures with or prediction of the molecular type of retinitis pigmentosa may be provided in embodiments. This instance and others indicate that disease related to some gene defect may produce a characteristic visual field loss. Even if it is not possible to predict disease by gene defect, through study of multiple subjects with the same disease at the molecular level, a field loss may be discernible that may suggest a deficiency or defect of certain classes of genes or a similar pathway of tissue dysfunction and eventual cell death.

FIGS. 20A-H illustrate exemplary volumetric measurements of the HOV for the right eye of a normal subject in accordance with various embodiments. FIGS. 20A (top left) and 20B (top right) show en face and side views of the HOV of a normal subject using the W187 grid and the size III test target. FIGS. 20C (second row, left) and 20D (second row right) illustrate use of a selection tool within VFMA to measure the volume of the entire HOV (depicted in 20D). By using the selection tool within VFMA, one may measure the volume of the entire HOV, which in this instance is 65.95 decibel-steradians. FIGS. 20E (third row, left) and 20F (third row, right) show side views of the selection shown in FIGS. 20C and 20D, respectively. FIGS. 20G (bottom row, left) and 20H (bottom row, right) show additional side views of the selection shown in FIGS. 20C and 20D, respectively.

FIGS. 21A-H illustrate exemplary three-dimensional graphs of the HOV for the left and right eyes of a subject with RP, in accordance with various embodiments, showing sensitivity. FIGS. 21A (top row, left) and 21B (top row, right) show en face views of the HOV for the left and right eyes, respectively, of a subject with RP. FIGS. 21B (second row, left) and 21C (second row, right) show side views of the HOV for the left and right eyes, respectively, of a subject with RP. FIGS. 21E (third row, left) and 21F (third row, right) show use of a selection tool within VMFA to measure the volume of the HOV for the left and right eyes, respectively, of a subject with RP. By using the selection tool within VFMA, one may with a cursor outline the field and measure the volume of the entire HOV, which in this instance is 19.05 decibel-steradians for the left eye and 15.82 decibel-steradians for the right eye. This measurement of the HOV represents an extremely useful variable that may be used to define the sensitivity of an eye in health and disease, for monitoring of disease during treatment or for potential retinal toxicity, and as an endpoint in clinical trials.

Figure 22A:
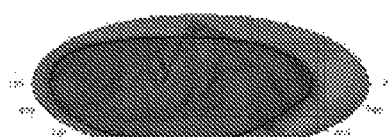
FIGS. 22A-F are panels depicting the tilt and side views of the selection of the HOV shown in FIGS. 21E (left) and 21F (right), in accordance with various embodiments.
Figure 22B:
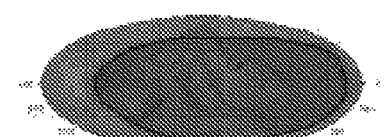
Figure 22C:
Figure 22D:
Figure 22E:
Figure 22F:

FIGS. 22A-F depict the tilt and side views of the selection of the HOV shown in FIGS. 21E (left) and 21F (right) in accordance with various embodiments. FIGS. 22A (top row, left) and 22B (top row, right) show tilt views of the selected HOV for the left and right eyes, respectively, of a subject with RP. FIGS. 22C (middle row, left) and 22D (middle row, right) show side views of the selected HOV for the left and right eyes, respectively, of a subject with RP. FIGS. 22D (bottom row, left) and 22E (bottom row, right) show side views of the HOV for the left and right eyes, respectively, of a subject with RP.

Figure 23A:
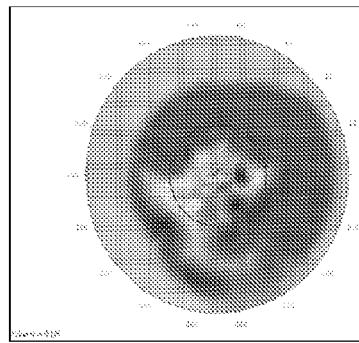
Figure 23B:
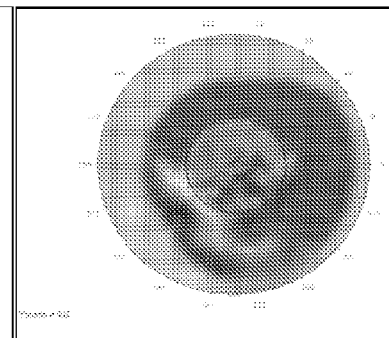
Figure 23C:
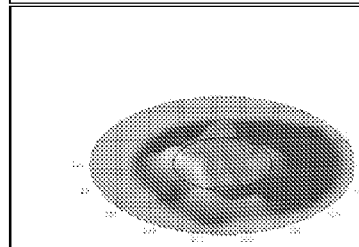
Figure 23E:
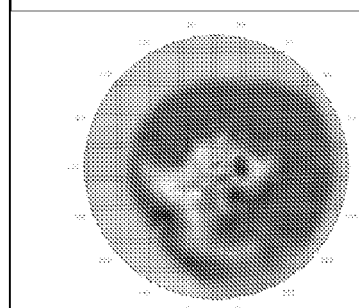
Figure 23F:
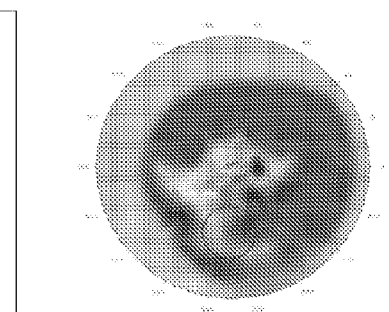

FIGS. 23A-E show use of a selection tool within VMFA to determine volumetric measurements of specific areas of the HOV and for mathematical signatures on these selections, in accordance with various embodiments. FIGS. 23A (top row, left) and 23B (top row, right) show selection of circles within a visual field. The selection tool may be used to determine volumetric measurements of specific areas of the HOV and for mathematical signatures on the selected areas. This figure shows how circles of the visual field may be selected. The volume of the selection is 9.05 decibel-steradians. FIGS. 23C (second row, left) and 23D show side views of the selection shown in FIGS. 23A and 23B, respectively. FIGS. 23E (third row, left) and 23F (third row, right) show use of the selection tool to place similar sized circles in different areas of the HOV to measure the sensitivity in those regions, in accordance with various embodiments. Here, the selection tool was used to place similar sized circles in different areas of the HOV to measure the sensitivity in these regions, which was 0.01 decibel-steradian for the right eye and 1.80 decibel-steradians for the left eye.

FIG. 23G (bottom row, center) shows a measurement of a specific area within the HOV. This is another example of measurement of a specific area within the HOV for the left eye, which measured 0.21. The ability to precisely measure regions of the HOV may be extremely valuable, for instance, for monitoring gene directed therapy delivery to the retina. For example, a subretinal injection may be administered that just encompasses the circle above. If following an appropriate observation period, the sensitivity for this selected area increases substantially, this would be a powerful means of validating that sensitivity was benefited because of the gene delivery. The ability to obtain numerical measures that reflect regions of the visual field provides an important endpoint for clinical trials of treatments that target selected areas of the retina.

Embodiments also provide for the determination of the effect of age and sex on measures of the HOV and test-retest variability. Using the slightly smaller W158 grid, with 158 instead of 187 points, the effect of age and gender on all measurement parameters and test-retest variability for both normal subjects and for subjects with RP may be determined.

In embodiments, techniques for modeling of the visual field and the development of the signatures and evaluation parameters may greatly aid the study of visual field defects over time and provide information about which areas of the retina are most susceptible to the progression of retinal dysfunction, information that may lead to new insights into mechanisms of cone loss in RP. These mathematical functions and measurements may be used to develop parameters that may be applied to the early diagnosis and characterization of RP by field type and for quantifiable endpoints to follow clinical therapeutic trials. The study of statokinetic dissociation using mathematical modeling is important for RP because it provides insights into underlying mechanisms of retinal damage, in particular the type of damage that leads to greater loss of retinal sensitivity to stationary test targets than to moving test targets. This knowledge may enable better interpretation of how disease affects function within different layers of the retina and may aid in the design of clinical trials by enabling testing for how treatment strategies influence these differences.

Figure 24A:
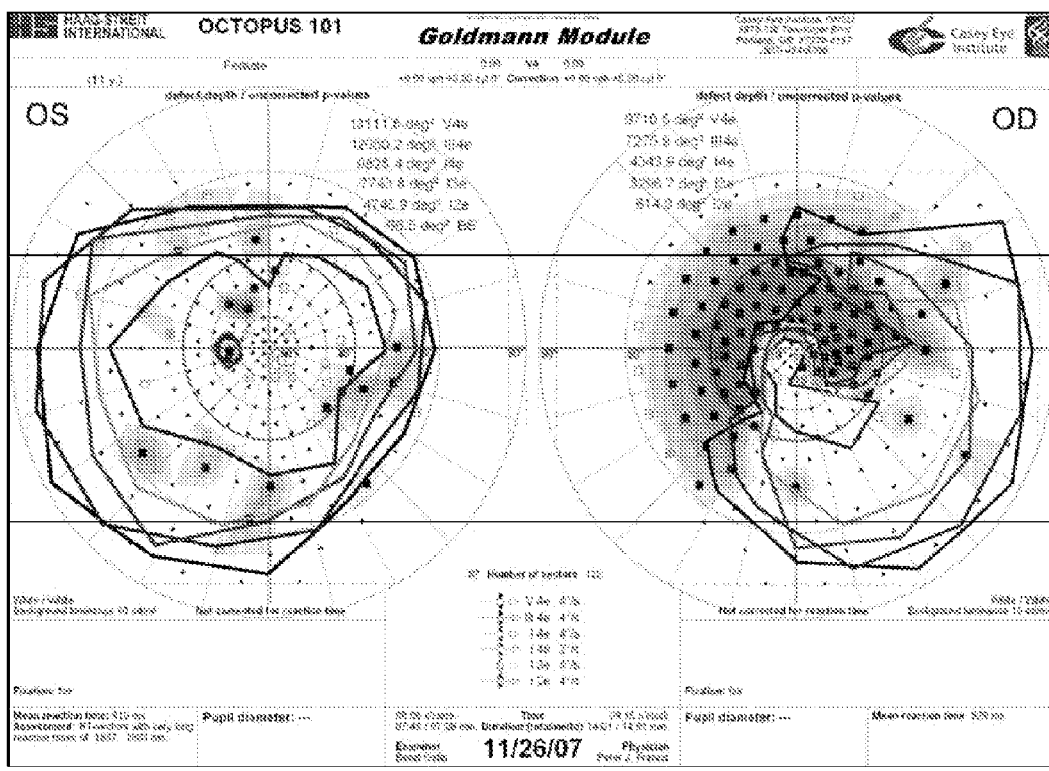
FIGS. 24A-E are panels illustrating views within VMFA of secondary pigmentary retinopathy from Diffuse Unilateral Subacute Neuroretinitis (DUSN) in a 11-year-old girl with retinopathy affecting only one eye, in accordance with various embodiments.
Figures 24B, 24C:
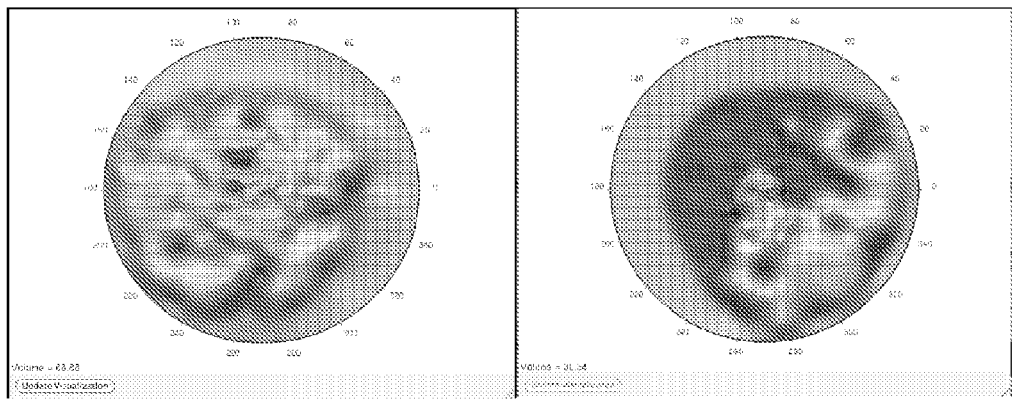
Figures 24D, 24E:
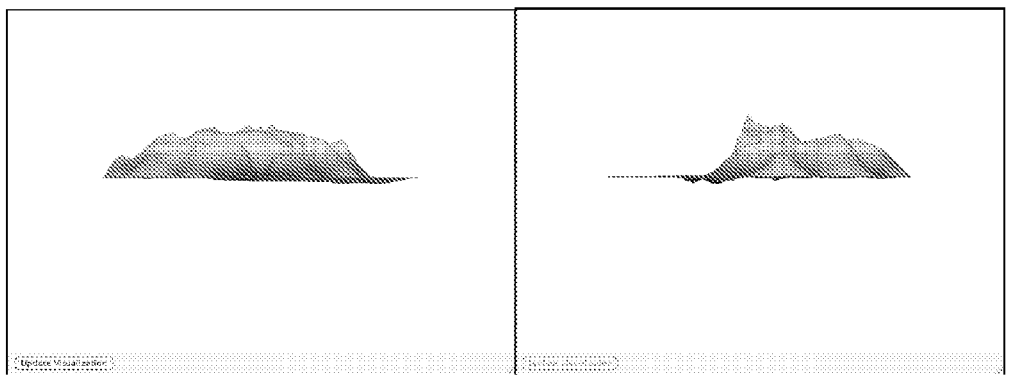

FIGS. 24A-E illustrate views within VMFA of secondary pigmentary retinopathy from Diffuse Unilateral Subacute Neuroretinitis (DUSN) in an 11-year-old girl, with retinopathy affecting only one eye, in accordance with various embodiments. The abrupt transition from very abnormal retinal sensitivity to normal or near normal sensitivity and the agreement of static and kinetic perimetry denote the absence of the phenomenon of statokinetic dissociation, which supports a diagnosis of non-genetic retinopathy secondary to inflammatory disease. This most likely was related to prior systemic infection with an organism that caused inflammation and secondary retinal degeneration, significantly affecting only the left eye. FIGS. 24B (left) and 24C (right) illustrate en face views of the HOV for the same subject. FIGS. 24D (left) and 24E (right) illustrate side views of the HOV for the same subject.

Figure 25:
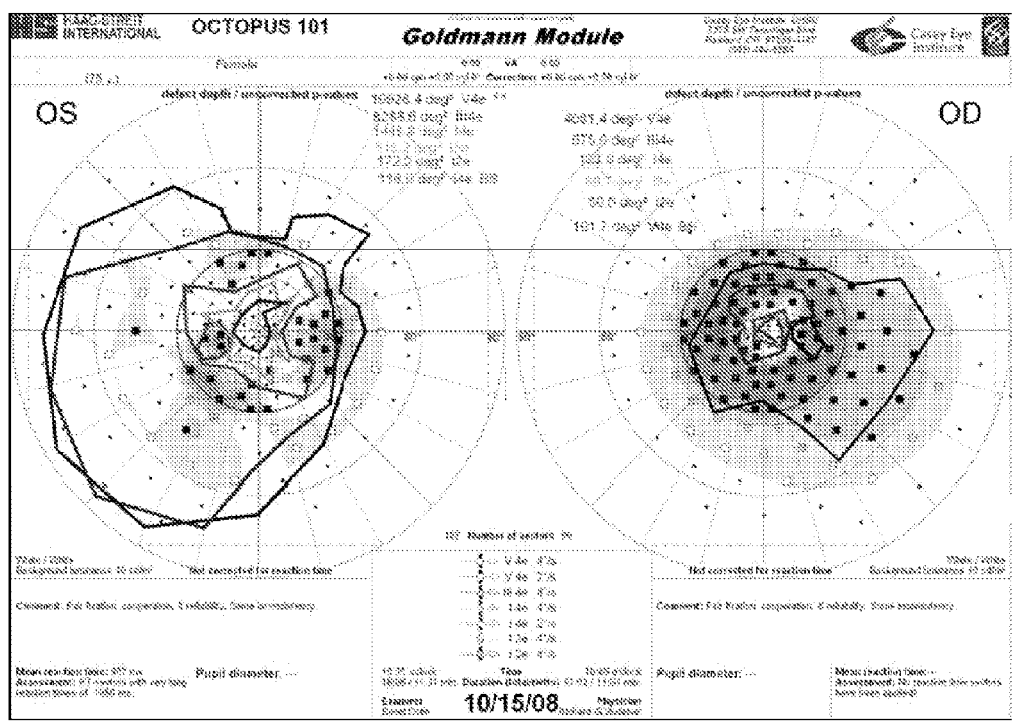
FIG. 25 shows a static perimetry visual field within VMFA of a 75-year-old subject, in accordance with various embodiments, showing secondary retinal degeneration from toxicity and with the right eye showing more degeneration and substantial tunnel vision.

FIG. 25 shows an exemplary static perimetry visual field within VMFA of a 75-year-old subject in accordance with various embodiments, showing secondary retinal degeneration from toxicity and with the right eye showing more degeneration and substantial tunnel vision. The subject took hydroxychloroquine for many years for rheumatoid arthritis, resulting in secondary retinal degeneration from toxicity from this medication. The right eye is much more involved with the degeneration and has substantial tunnel vision, with the field more constricted to static testing than for kinetic testing. This is an example of statokinetic dissociation that likely results from the damage to the retinal pigment epithelium with additional damage to the overlying photoreceptors.

Figure 26:
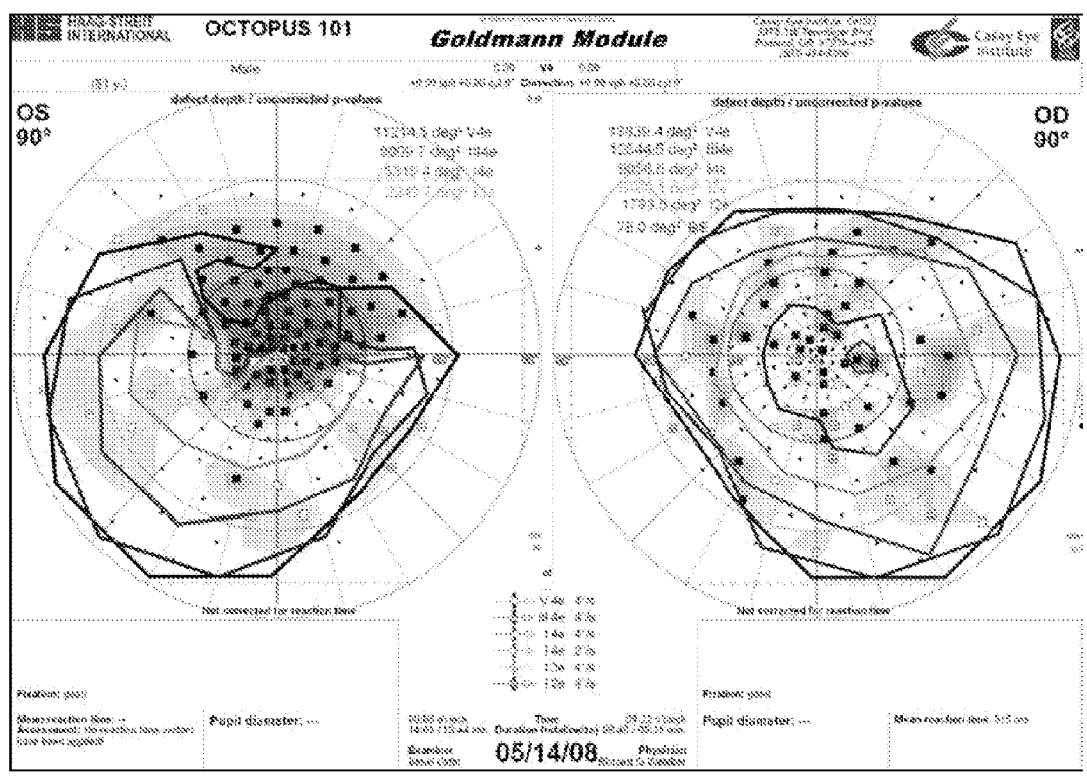
FIG. 26 shows a static perimetry visual field within VMFA, in accordance with various embodiments, of a 51-year-old subject with colobomatous optic nerves and glaucoma with greater damage to the left eye, which shows arcuate defects extending to the periphery superiorly.

FIG. 26 shows an exemplary static perimetry visual field within VMFA, in accordance with various embodiments, of a 51-year-old subject with colobomatous optic nerves and glaucoma with greater damage to the left eye, which shows arcuate defects extending to the periphery superiorly.

FIGS. 27A-E show exemplary views of a static perimetry visual field and HOV within VMFA of a 31-year-old subject after neurosurgical removal of a large pituitary tumor that had compressed the chiasm, causing a complete bitemporal hemianopsia, using a size III test target in accordance with various embodiments. Neurosurgical removal of the tumor was performed four months previously, and some recovery of temporal field is becoming evident now when tested with the size III test target. Also, the size V test target demonstrates much more recovery (see FIG. 28A-E, below). This is a very favorable sign that may indicate a favorable prognosis, and indeed, six months later, the visual fields recovered to near normal. The three-dimensional plots, views, and signatures provide novel information that may provide insight into the nature of the field defects. Volumetric measurements may be used to assess recovery and final outcomes. FIGS. 27A-E use the size III test target for the static perimetry. In some examples, the smaller test target does not measure well very low levels of sensitivity and thus testing with this size target suggested a near complete bitemporal hemianopsia only marginally better than prior to surgery.

FIGS. 28A-E show exemplary views of a static perimetry visual field and HOV within VMFA of the same 31-year-old subject using a size V test target, which may be used to measure lower levels of sensitivity within a field of vision in accordance with various embodiments. There is substantially greater recovery of the inferotemporal visual field using this test target size. This indicates that substantial potential for further recovery exists.

Figure 29D:
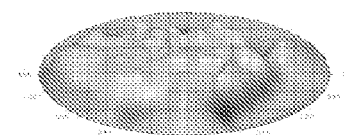
Figure 29E:
Figure 29F:
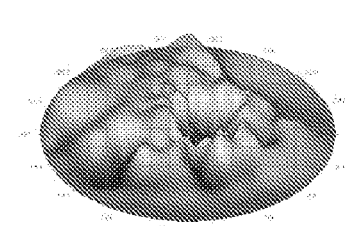
Figure 29G:
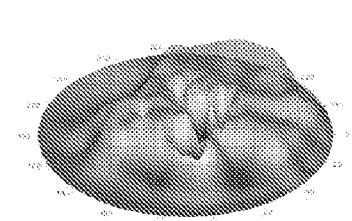
Figure 29H:
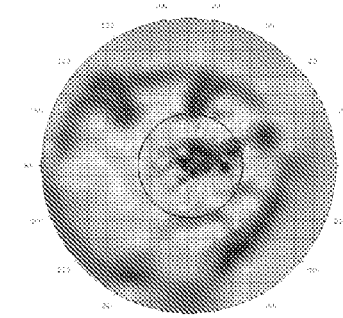
Figure 29I:
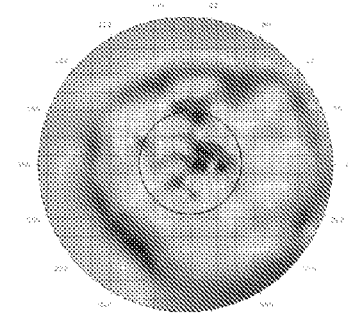
Figure 29J:
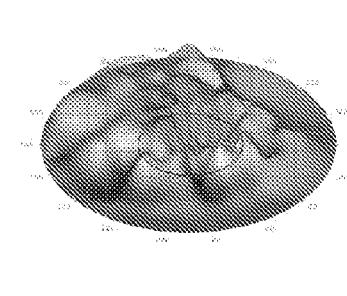
Figure 29K:
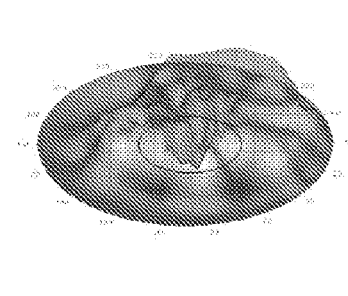

FIGS. 29A-M show graphs from a subject with Leber Hereditary Optic Neuropathy, demonstrating how the three-dimensional plots and signatures provided by various embodiments provide additional information helpful to understanding disease at the visual field defect level. This subject had sudden, severe loss of vision first in one eye and then the other. Three-dimensional plots show the defects of the central field with decreases in sensitivity elsewhere as well. FIGS. 29J (bottom row, left) and 29K (bottom row, right) show the underside of the HOV and the sensitivity losses within the central field from the disease for the left and right eye, respectively, and FIGS. 29L (left) and 29M (right) show Mercator projections and signatures within VMFA showing sensitivity losses from the disease for the left and right eye, respectively, in accordance with various embodiments.

FIG. 30 shows an exemplary static perimetry visual field within VMFA of a subject with both glaucoma and autoimmune retinopathy, for which three-dimensional modeling and analysis of signatures provided by various embodiments offers the ability to quantitate the loss of vision from each component of this person's disease. The Mercator projection and signatures indicated mid and far peripheral retinal disease beyond the arcuate defect superiorly in the left eye. Such separation of components of disease may be valuable to monitor selective treatments of complex disorders such as this.

Figure 31:
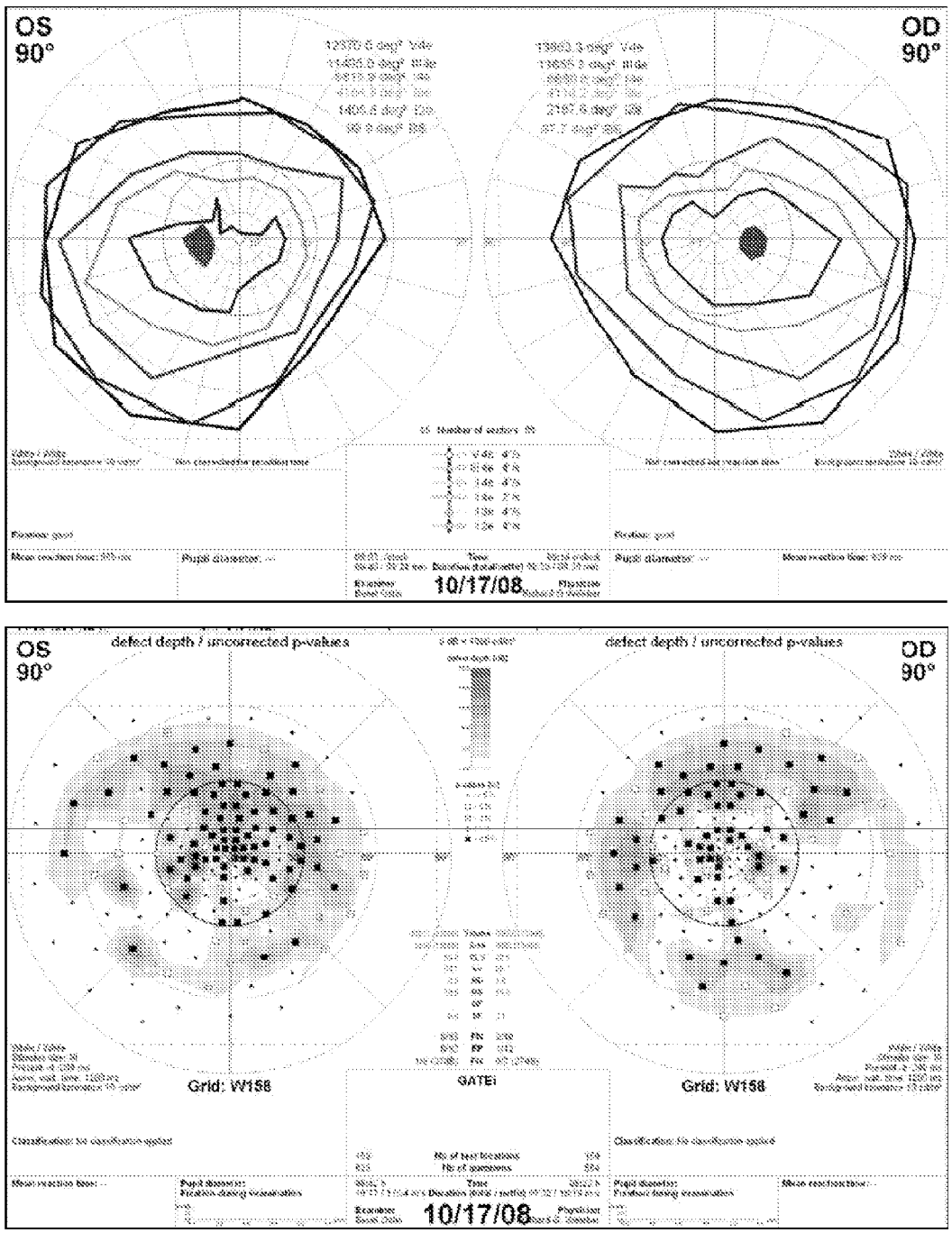
FIG. 31 shows kinetic perimetry (top) and static perimetry (bottom) of a subject with ABCA4-related maculopathy (Stargard/Fundus Flavimaculatus) with losses of peripheral as well as central sensitivity, in accordance with various embodiments; the kinetic perimetry is rather non-revealing, whereas the static visual fields are very abnormal.

In another example, FIG. 31 shows kinetic perimetry (top) and static perimetry (bottom) of a subject with ABCA4-related maculopathy (Stargard/Fundus Flavimaculatus) with losses of peripheral as well as central sensitivity. The kinetic perimetry is rather non-revealing, whereas the static visual fields are very abnormal.

FIGS. 32A-D show exemplary graphs within VMFA from the same subject as in FIG. 31, illustrating the HOV in the subject's left (FIG. 32A, top left) and right (FIG. 32B, top right) and the corresponding Mercator projections and signatures (FIG. 32C, bottom left, and FIG. 32D, bottom right, respectively). The three-dimensional modeling, measurements of the HOV, and signatures may be valuable for characterization and to serve as endpoints for clinical trials in macular dystrophy, such as Stargard/Fundus flavimaculatus, as well as age-related macular degeneration.

In other embodiments, normal values for the volumetric measurement of the HOV are provided, both for the total visual field and for the central 30-degree field. Such new volumetric measures may return more detailed modeling of the volume of the HOV, as well as enable new measurements of the difference between the volume of the HOV of a subject and that of an age-specific smooth model of the normal HOV created from data derived from tests on normal subjects of various ages.

Figure 33:
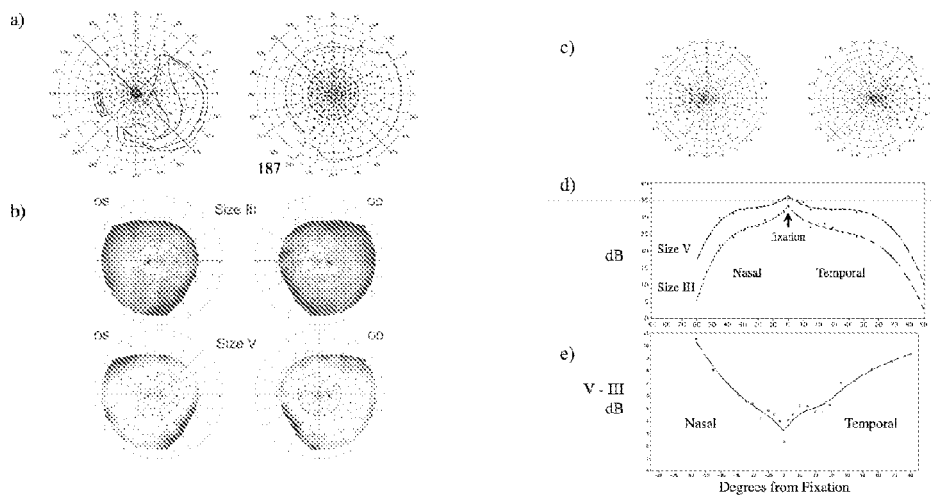
FIG. 33 illustrates the design of the grids, illustrates the finding of greater sensitivity using the size V than the size III test target as described above, and displays the DLS values by eccentricity from the fovea, as well as the differences between size V and size III for the difference degrees from fixation, in accordance with various embodiments. The nasal and, to a greater extent, temporal curves plateau to a greater extent, particularly for the size V test target.

FIG. 33 illustrates exemplary "defect" section templates. Defect modeling may be useful for characterizing and measuring the global and regional variations of the volumetric measures of the HOV in a subject compared to the appropriate normal smooth spline-fit age-adjusted model, which is derived from pooled data collected from age-matched normal subjects. An example of the usefulness of defect modeling is the definition, characterization, measurement, and volumetric measurement of a scotoma, either central or anywhere in the visual field. These volumetric measurements of portions of the HOV may be important for use in clinical trials, for example as endpoints in therapeutic trials for Stargardt disease and age-related macular degeneration.

In embodiments, defect modeling utilizes the differences between the differential sensitivity (DLS) values for the subject and age-corrected DLS values to create a set of derived values that represent point-by-point exactly where and by how much the subject's HOV differs from normal. In various embodiments, it is this set of subtracted DLS values that, when modeled, may depict the true differences related to disease. Examination of the surface of this new model and determination of the volume underlying this three-dimensional surface may enable accurate and valid topographic representation of localized defects.

For all three models, the subject data, the normal data, and the subtracted data that are used to model the defect data, a variety of options may be available to automatically create selections or templates to measure the HOV for the entire test grid used (or, at least, that portion of the true HOV that is tested by the extent of the grid) or, through automatically or manually positioned circles or free-hand-drawn selections that will measure any portion of the HOV. In embodiments, the base and extent of a scotoma or other defect space may be selected. These functions of specific selection tools on the defect space may allow the accurate, precise, and reproducible measurement of scotomas. In certain examples, a three-dimensional model representation of the defect surface may be created by mathematically subtracting the two models of the HOV, that of the subject and that of the normal smooth-model (spline-fit) HOV representation, without first going through the step of subtracting the raw DLS values of the subject from those of the normal subjects. Working within the confines of the two mathematical models rather than the raw DLS values may reduce lost information from the complete models and offers even greater precision, validity and accuracy in the detection, characterization, and measurement of the space of the HOV, both for diagnosis and for generating of endpoints for clinical trials.

FIG. 33 illustrates the design of the grids and the finding of greater sensitivity using the size V than the size III test target as described above, and displays the DLS values by eccentricity from the fovea, as well as the differences between size V and size III for the difference in degrees from fixation, in accordance with various embodiments. In embodiments, the nasal and, to a greater extent, temporal curves plateau to a greater extent, particularly for the size V test target.

Figure 34:
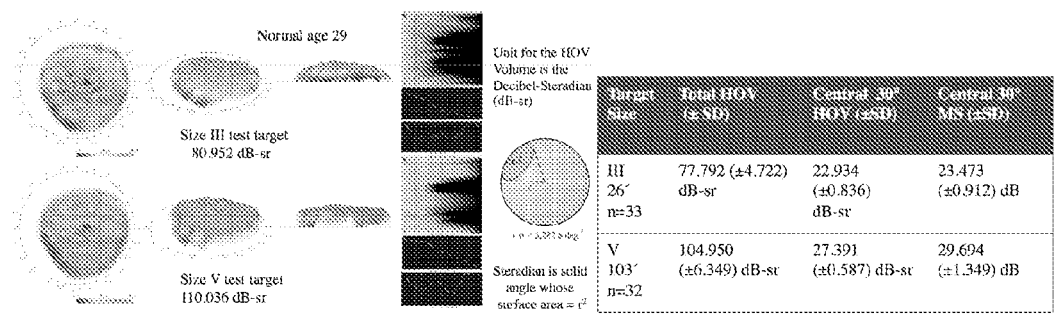
FIG. 34 depicts the HOV for a normal 29-year-old subject with the volumetric measurements of the HOV in decibel-steradians, in accordance with various embodiments.

FIG. 34 depicts the HOV for a normal 29-year-old subject with the volumetric measurements of the HOV in decibel-steradians, in accordance with various embodiments. The table presented on the right of FIG. 34 illustrates the values for the mean and standard deviation of the volume of the total HOV and that for only the central 30 degrees of normal subjects (mean age of approximately 28 years for size III [n=33] and size V [n=32] test).

Figure 35:
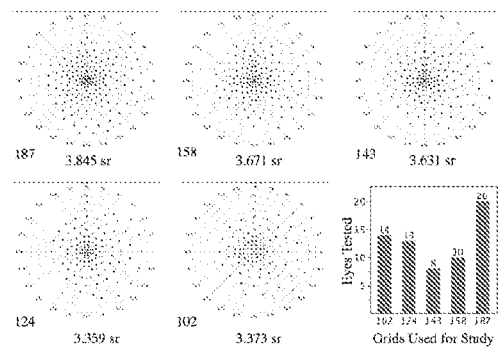
FIG. 35 illustrates the relationship between the number of points in the grids and the resultant volumetric measures of the HOV, in accordance with various embodiments.

In another example, FIG. 35 illustrates the relationship between the number of points in the grids and the resultant volumetric measures of the HOV, in accordance with various embodiments. Even the largest grid used cannot measure all of the HOV in all normal individuals (there is considerable variability in the volume of the HOV among normal subjects). The final selection of the number of points and their distribution is, in general, a compromise between achieving the desired resolution of detail for small scotomas or defect areas and field loss of more irregular shape and the greater time it takes to actually test subjects with grids of larger numbers. The grids that had the larger number of test locations also subtend larger solid angles in steradians and, hence, cover a greater portion of the visual field (and, subsequent, the HOV). The linear regression analysis of the volume of the HOV versus number of test locations in each grid was insignificant (p=0.09) for the size III test target and only reached a marginally significant p-value (0.05) for size V test target for the total HOV but not for either the volumetric measure of the central 30 dg field or the Mean Sensitivity (p-values >0.21). However, when the truncating effect of the differences in solid angle for the grids is taken into consideration, all variables, including the total HOV, become unrelated (r2 was 0.13 at p=0.45 for size III and r2 was 0.059 at p=0.21 for size V) to the number of test loci in the grids.

Figure 36:
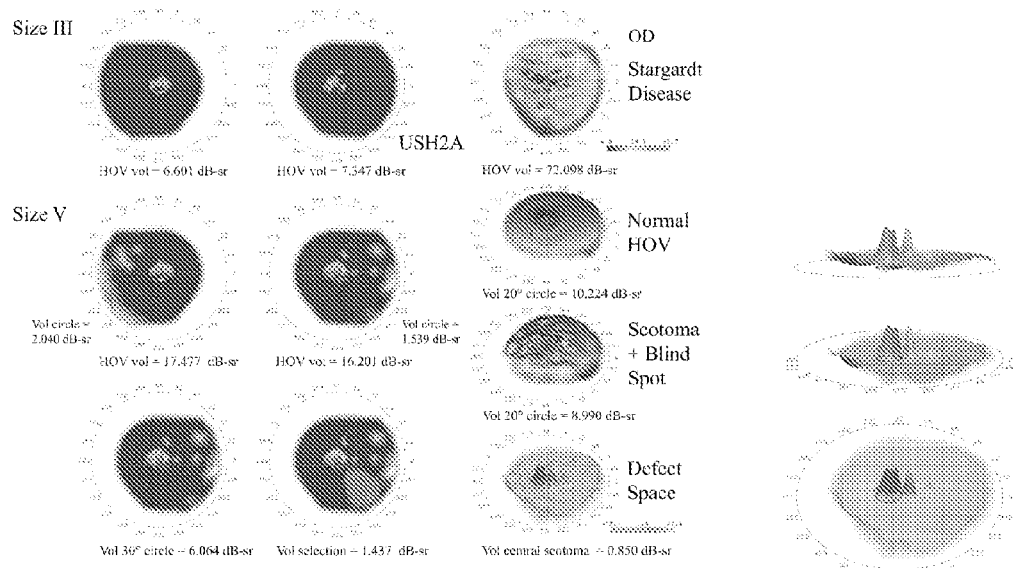
FIG. 36 illustrates, for the left and right eyes of a 21-year old subject with USH2, the various measures of the HOV of size III and V static DLS values, through template selections automatically generated from the outer perimetry of the grid pattern (top left and middle figures), in accordance with various embodiments.

FIG. 36 illustrates, for the left and right eyes of a 21-year old subject with USH2, various exemplary measures of the HOV of size III and V static DLS values, through template selections automatically generated from the outer perimetry of the grid pattern (top left and middle figures), in accordance with various embodiments. In some embodiments, with the size III test target, there is virtually no discernible sensitivity outside the central 10-15 dg region. In other embodiments, with the size V test target (middle left and center), there is greater sensitivity centrally and there exists measureable sensitivity in the temporal and inferior fields, mostly toward the periphery. The lower left and middle images and the lower middle image depict the assessment of the HOV for the right eye by use of circle or free-hand selections placed in the HOV to simulate areas that might be treated with a unilateral therapy such as a gene replacement strategy, which may be an appropriate strategy for use for a unilateral treatment. Comparison of the total HOV (16.201 dB-sr) for the middle center three-dimensional model with that portion of the HOV that resides only within the central field (6.064 dB-sr, as shown in the lower left figure) illustrates that, for this right eye, the field outside of the central 30 degrees is approximately 2.7 that volume (in dB-sr) within the central 30 degrees.

Referring to FIG. 36, the four illustrations on the middle right and the three images to the far right depict exemplary volumetric measurements of the right eye of a subject with Stargardt Disease. The total HOV in this eye (top image) with Stargardt disease is 72.098 dB-sr, which is 5.694 dB-sr less than the normal of 77.792 dB-sr. Clearly, this 5.694 dB-sr value is a volumetric that includes many defects both centrally and peripherally. A 20° circle selection of the HOV of a normal spline gave a volumetric measurement of 10.224 dB-sr, whereas the same circle selection on the subject's HOV returned a volume of 8.990. The difference of 1.234 dB-sr between these two measures includes both the blind spot and the central scotoma, as well as more subtle defects in the central portion of the HOV. The most specific assessment of the central scotoma may be measured from the inverted scotoma on the defect space, which is created by subtracting the subject's HOV from the normal HOV. This volume, which is 0.850 dB-sr for this eye, may represent a suitable endpoint for clinical trials. Three larger tilted images of inverted central scotoma are shown on the far right.

As discussed above, in various embodiments, tools that may be used to automatically select the base of the inverted scotoma to be measured remove any subjective aspect of the hand-drawn selections and lead to more reproducible endpoints. In one exemplary embodiment, a method to identify with precision and accuracy the boundary of the scotoma is to use the first derivative of change in slope of the base of the inverted scotoma. This identifies the region where the slope change is greatest. In embodiments, this strategy first generates an average base value of the defect surface surrounding the scotoma of interest so that the outer boundary of the base of the scotoma may be identified by either a fixed set dB deviation from this base or by deviation from the base by a set statistical amount, such as by a confidence interval, such as a 95% confidence value or by a specific criterion value based on the standard deviation. These strategies may access the noise in the defect surface and calculate a probability of accuracy and validity for the defect volume. In particular embodiments, the grids also may include sentinel points to test for midline field defects and nasal step field defects.

Figure 37:
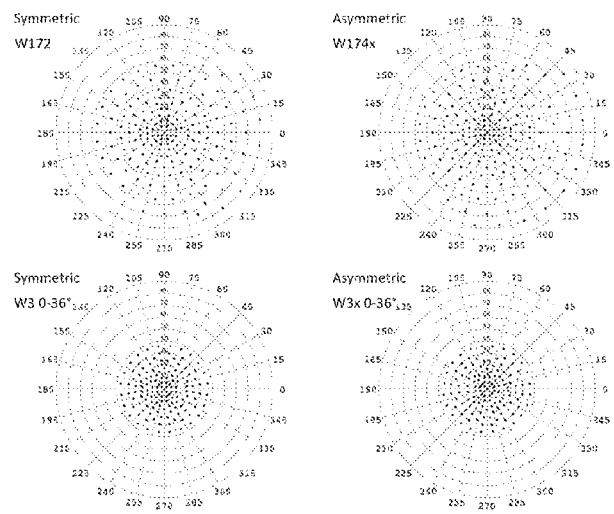
FIG. 37 illustrates binocular grids, in accordance with various embodiments.

Finally, in some embodiments, binocularly symmetric grids may be used to assess binocular vision as well as monocular vision. FIG. 37 illustrates exemplary binocular grids, in accordance with various embodiments. In some examples, the grids for monocular testing that are designed for the right eye may be flipped on a horizontal axis for use for the left eye. In embodiments, the symmetric grids are designed such that when flipped, the central portion of the grids contains test locations that occupy identical points in the field of vision when viewed with both eyes open. This congruity of test locations may allow the assessment of the normal increase in sensitivity that is observed in the overlapping portions of the field for the two eyes.

Figure 38:
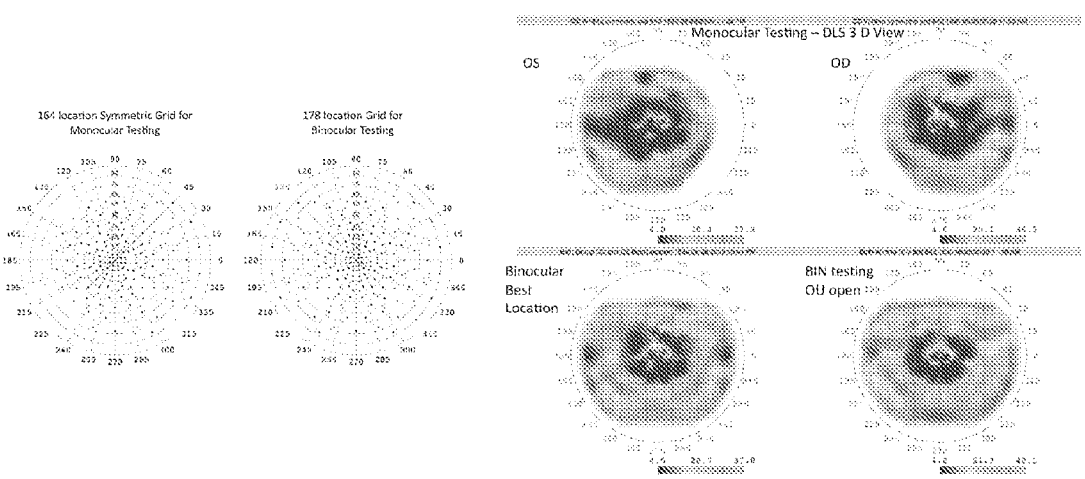
FIG. 38 illustrates binocular compensation, in accordance with various embodiments. The left panel depicts a symmetric 164-point grid and a corresponding 178-point binocular grid. The right panel depicts monocular testing (top) of a patient with type II Usher syndrome and binocular simulation and binocular testing (bottom).

In various embodiments, the binocular grids may be used to assess the binocular compensation between the two eyes. In embodiments, this test may be used, for examples, for the determination whether or not individuals might qualify to drive or work at specific jobs when they have significant defects that, when tested monocularly, might disqualify them. Severe monocular field loss may be compensated because the field loss affects different portions of the field between the eyes and with binocular use of both eyes and normal binocular summation, the field with both eyes open is much more intact than with either eye alone. FIG. 38 illustrates binocular compensation, in accordance with various embodiments. In FIG. 38, the left panel depicts a symmetric 164-point grid and a corresponding 178-point binocular grid. The right panel depicts monocular testing (top) of a patient with type II Usher syndrome and binocular simulation and binocular testing (bottom). In various embodiments, binocular summation is a very important physiologic phenomenon in vision whereby, within the central portion of the visual field that overlaps between the two eyes, the sensitivity in this central region when tested binocularly is increased up to 15% of that sensitivity when tested monocularly. Disturbances of binocular summation can alter the quality of visual sensation.

Disturbances of binocular summation can occur with disease at any level of the visual system, but is particularly notable with disease or injury of the retina, optic nerve, optic chaism, optic tracts, optic radiations, or visual cortex. A particularly important acquired disease, that of blunt injury to the visual cortex, as part of traumatic brain injury, can disturb binocular vision without the subject being aware of this change. Traumatic Brain Injury (TBI) is a very suitable disorder to use visual field modeling comparing predicted and actual binocular summation to assess the effects of the trauma on the normal expected increase. Reaction times may also be assessed and, if kinetic testing is also performed, statokinetic dissociation may be assessed.

Figure 39:
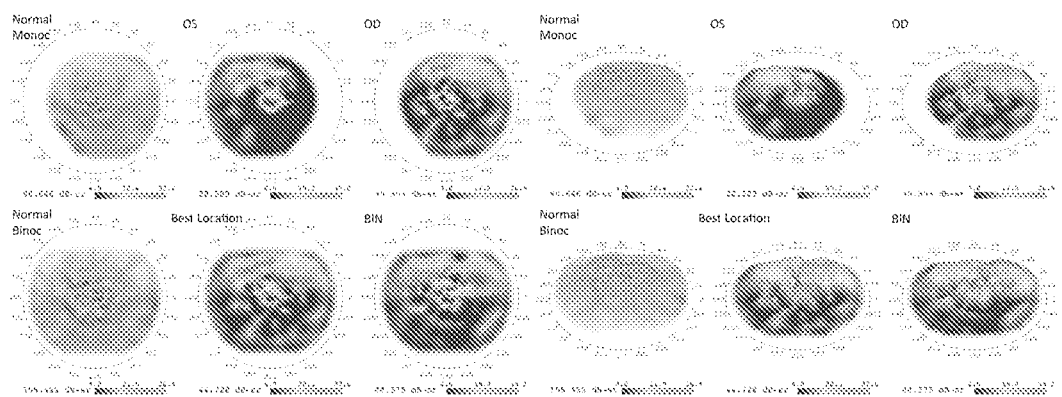
FIG. 39 illustrates monocular and binocular testing of the visual field for a subject with autosomal dominant RP, in accordance with various embodiments.

The lower left of the right panel in FIG. 38 depicts the simulation of binocular vision by combining visual fields of OS and OD using the best sensitivity at each test site (Binocular Best Location), which closely approximates the binocular visual field with both eyes tested simultaneously (BIN testing OU open). Simulation has also been modeled, in various embodiments, using probability summation (using the square root of the sum of squares of right and left eye sensitivity at each test site). FIG. 39 illustrates monocular and binocular testing of the visual field for a subject with autosomal dominant RP, in accordance with various embodiments. Monocular testing of the field of each eye did not qualify him to drive a car, but binocular testing disclosed sufficient field to meet the criterion for licensing.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for mapping a Hill of Vision for a subject, comprising:
    importing threshold data from an input source;
    converting the threshold data to constraints on a spline surface with an algorithm to create a three-dimensional representation of the Hill of Vision; and
    displaying one or more three-dimensional representations of the Hill of Vision.

2. The method of claim 1, wherein the input source is a computing device.

3. The method of claim 2, wherein the computing device is a visual field testing device.

4. The method of claim 3, wherein the visual field testing device is a perimeter.

5. The method of claim 1, wherein the threshold data comprises static sensitivity data.

6. The method of claim 5, wherein importing threshold data from an input source comprises collecting static sensitivity data using one or more grids that have one or more of the following characteristics:
    polar-orientation of test locations;
    central condensation of test locations;
    rectilinear distribution of test locations; and
    sentinel points to test for midline field defects and nasal step field defects.

7. The method of claim 6, wherein collecting static sensitivity data using a polar-oriented grid comprises collecting static sensitivity data across a full field using a range of grid points.

8. The method of claim 6, further comprising using a Size V test target to collect the static sensitivity data.

9. The method of claim 6, wherein the one or more grids comprises a grid having a polar-orientation of test locations which comprises of binocularly symmetrical grids, and wherein converting the threshold data to constraints on a spline surface with an algorithm comprises performing binocular summation.

10. The method of claim 1, wherein the algorithm is an infinitely differentiable spline, and wherein the algorithm is not constrained by any interval between grids or any orientation of grids.

11. The method of claim 1, wherein the spline is a thin-plate spline.

12. The method of claim 1, wherein the three-dimensional representation is displayed in volume units.

13. The method of claim 10, wherein the volume units are decibel-steradian units (dB-sr).

14. The method of claim 1, further comprising taking a volume measurement of the three-dimensional representation of the Hill of Vision.

15. The method of claim 14, wherein taking a volume measurement of the three-dimensional representation of the Hill of Vision comprises taking a volume measurement for an entire three-dimensional representation of the Hill of Vision.

16. The method of claim 15, further comprising diagnosing or prognosing a visual system condition using the Hill of Vision volume measurement.

17. The method of claim 16, wherein the visual system condition comprises retinitis pigmentosa, macular degeneration, Usher syndrome, retinopathy, pigmentary retinopathy, diffuse unilateral neuroretinitis, retinal degeneration from toxicity, glaucoma, optic nerve disease, Leber hereditary optic neuropathy, maculopathy, or injury to the retina or optic nerve.

18. The method of claim 16, wherein diagnosing or prognosing the visual system condition comprises using a mathematical signature based on Mercator, Radial-Fourier, Bessel, or fractal mathematical deconvolution of the Hill of Vision volume measurement.

19. The method of claim 14, wherein taking a volume measurement of the three-dimensional representation comprises taking a volume measurement for a portion of the three dimensional representation of the Hill of Vision.

20. The method of claim 1, further comprising subtracting the three-dimensional representation of the Hill of Vision from a control three-dimensional representation of a Hill of Vision to create a defect model, wherein the defect model measures the location of the field defect in the field of vision.

21. The method of claim 1, further comprising comparing the three-dimensional representation of the Hill of Vision to a control three-dimensional representation of a Hill of Vision to diagnose or prognose a visual system condition.

22. The method of claim 21, wherein the visual system condition comprises retinitis pigmentosa, macular degeneration, Usher syndrome, retinopathy, pigmentary retinopathy, diffuse unilateral neuroretinitis, retinal degeneration from toxicity, glaucoma, optic nerve disease, Leber hereditary optic neuropathy, maculopathy, or injury to the retina or optic nerve.

23. The method of claim 21, wherein the control three-dimensional representation of a Hill of Vision comprises at least one of the following:
    a three-dimensional representation of a Hill of Vision taken from a different subject not having a visual system condition;
    an averaged three-dimensional representation of a Hill of Vision taken from a group of subjects not having a visual system condition; and
    a three-dimensional representation of a Hill of Vision taken from the subject patient at a different time.

24. The method of claim 21, further comprising a computer-assisted classification scheme, and wherein the control three-dimensional representation of a Hill of Vision comprises a group of three-dimensional representations of Hills of Vision.

25. A tangible computer-readable medium having stored thereon, computer-executable instructions that, as a result of execution by a computing device, cause the computing device to perform a method for mapping a Hill of Vision for a subject comprising:
    importing threshold data from an input source;
    converting the threshold data to constraints on a spline surface with an algorithm to create a three-dimensional representation of a Hill of Vision; and
    displaying one or more three-dimensional representations of the Hill of Vision.

26. A method of determining a response to a therapy for a subject having a visual system condition, wherein the method comprises:
    mapping a first Hill of Vision of a subject at a first time point;
    administering the therapy;
    mapping a second Hill of Vision of the subject at a second time point after administration of the therapy; and comparing the first Hill of Vision to the second Hill of Vision, wherein mapping the first and second Hills of Vision comprises importing threshold data from an input source, and converting the threshold data to constraints on a spline surface with an algorithm to create a three-dimensional representation of the Hill of Vision.

27. A visual field testing device, comprising:

a perimetry testing device;

a processor configured to obtain threshold data from the perimetry testing device;

convert the threshold data to constraints on a spline surface with an algorithm to create a three-dimensional representation of the Hill of Vision; and compare the three dimensional representation of the Hill of Vision to a control three-dimensional representation of a Hill of Vision to diagnose or prognose a visual system condition.

\* \* \* \* \*